United States Patent
Zimak et al.

(10) Patent No.: US 11,992,569 B2
(45) Date of Patent: May 28, 2024

(54) ARRANGEMENT FOR INTRODUCING DECONTAMINATION AGENT INTO AN ENCLOSURE

(71) Applicant: Skan AG, Allschwil (CH)

(72) Inventors: Jean-Louis Zimak, Allschwil (CH); Volker Sigwarth, Sisseln (CH)

(73) Assignee: Skan AG, Allschwil (CH)

( * ) Notice: Subject to any disclaimer, the term of this patent is extended or adjusted under 35 U.S.C. 154(b) by 830 days.

(21) Appl. No.: 16/975,867

(22) PCT Filed: Feb. 21, 2019

(86) PCT No.: PCT/CH2019/000004
§ 371 (c)(1),
(2) Date: Aug. 26, 2020

(87) PCT Pub. No.: WO2019/165564
PCT Pub. Date: Sep. 6, 2019

(65) Prior Publication Data
US 2021/0069363 A1 Mar. 11, 2021

(30) Foreign Application Priority Data
Feb. 27, 2018 (EP) .................................. 18405007

(51) Int. Cl.
*A61L 2/22* (2006.01)
*A61L 2/24* (2006.01)

(52) U.S. Cl.
CPC ........ *A61L 2/22* (2013.01); *A61L 2/24* (2013.01); *A61L 2202/14* (2013.01); *A61L 2202/15* (2013.01)

(58) Field of Classification Search
CPC ..... A61L 2/00; A61L 2/16; A61L 2/18; A61L 2/22; A61L 2/24; A61L 2202/00; A61L 2202/10; A61L 2202/14; A61L 2202/15
See application file for complete search history.

(56) References Cited

U.S. PATENT DOCUMENTS

| 9,005,523 B2 * | 4/2015 | Hill ........................ A61L 2/186 422/50 |
| 2011/0266376 A1 | 11/2011 | Goessens |
| 2012/0224994 A1 * | 9/2012 | Steiner .................. B01D 53/79 422/111 |

FOREIGN PATENT DOCUMENTS

| CH | 689178 A5 | 11/1998 |
| CH | 699032 B1 | 1/2010 |

(Continued)

OTHER PUBLICATIONS

International Search Report of the International Searching Authority dated Jun. 24, 2019, along with an English translation, issued in connection with International Application No. PCT/CH2019/000004 (9 pages).

(Continued)

*Primary Examiner* — Natasha E Young
(74) *Attorney, Agent, or Firm* — McCarter & English, LLP

(57) ABSTRACT

The arrangement for introducing a desired quantity of decontamination agent into a containment facility comprises a tank as a storage vessel for storing the decontamination agent in liquid form. A metering apparatus having a spray nozzle is directed into the containment facility so as to atomize the decontamination agent. At least one feed line from the ambient air, a compressed air connection and a control unit are provided to operate the metering apparatus. The metering apparatus has a metering container that comprises a storage chamber that has a defined volume for receiving an individual portion of decontamination agent. The storage chamber is provided so as to successively receive a number (n) of portions of decontamination agent from the tank, and the portion respectively held in the storage chamber is introduced by means of the spray nozzle into the containment facility prior to receiving a subsequent portion.

20 Claims, 26 Drawing Sheets

(56) References Cited

FOREIGN PATENT DOCUMENTS

Figure 1A:
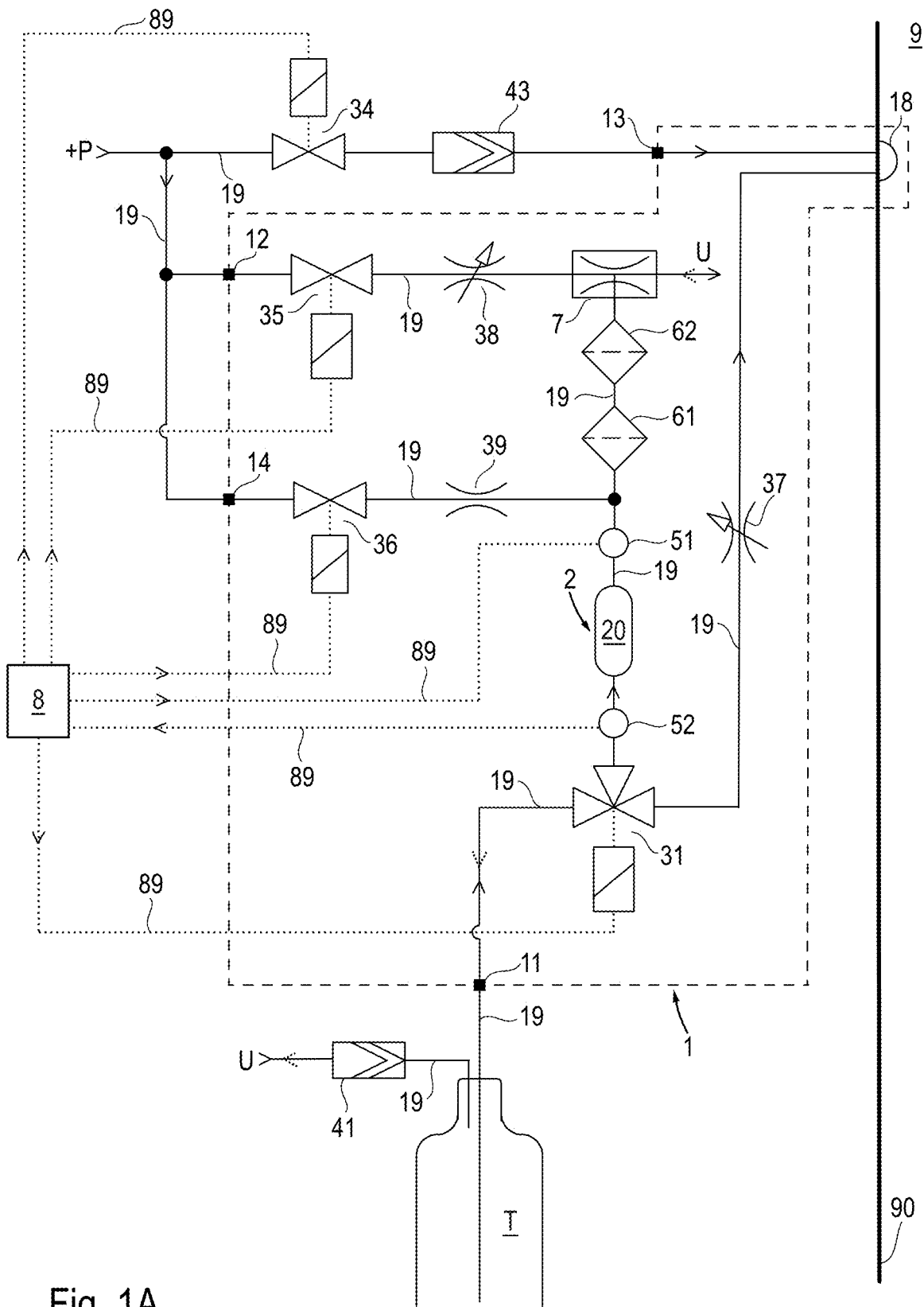

| EP | 1121942 A2 | 8/2001 |
|---|---|---|
| EP | 2692848 A1 | 2/2014 |
| EP | 2839845 A1 | 2/2015 |
| EP | 2889045 A1 | 7/2015 |
| WO | 94/07544 A1 | 4/1994 |
| WO | 2008/116341 A2 | 10/2008 |
| WO | 2013/003967 A1 | 1/2013 |

OTHER PUBLICATIONS

Written Opinion of the International Searching Authority dated Jun. 24, 2019, issued in connection with International Application No. PCT/CH2019/000004 (6 pages).

* cited by examiner

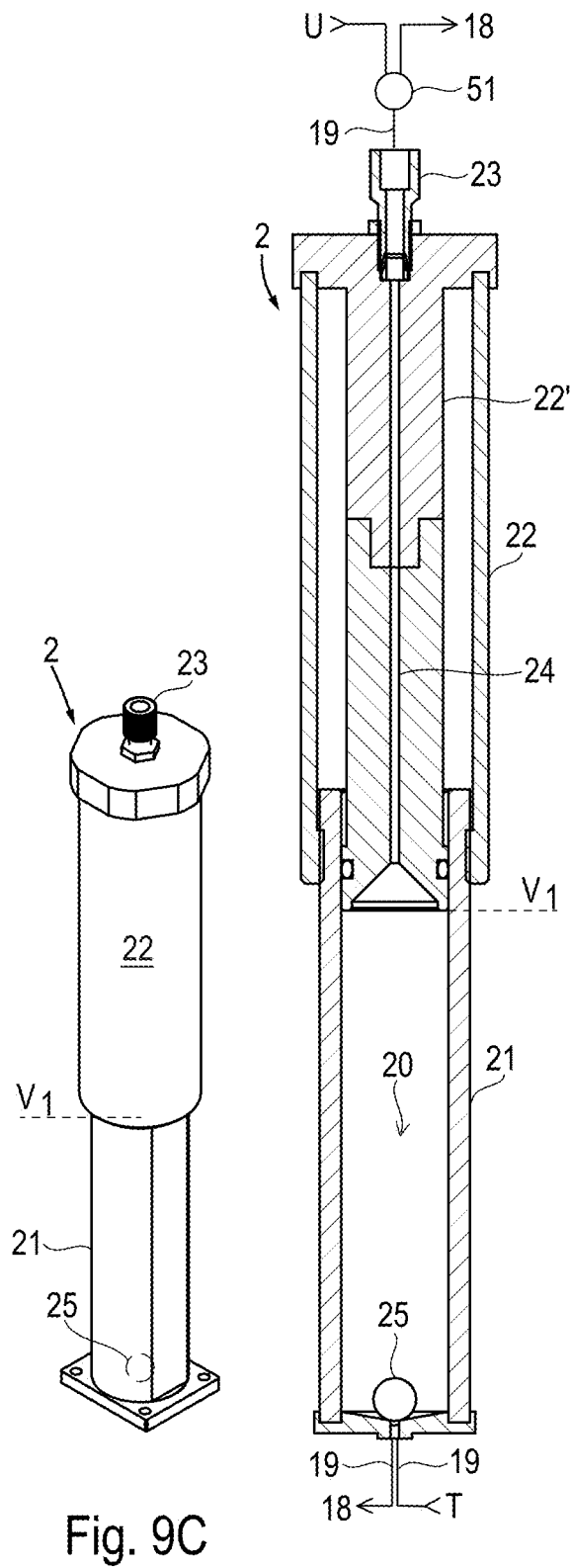
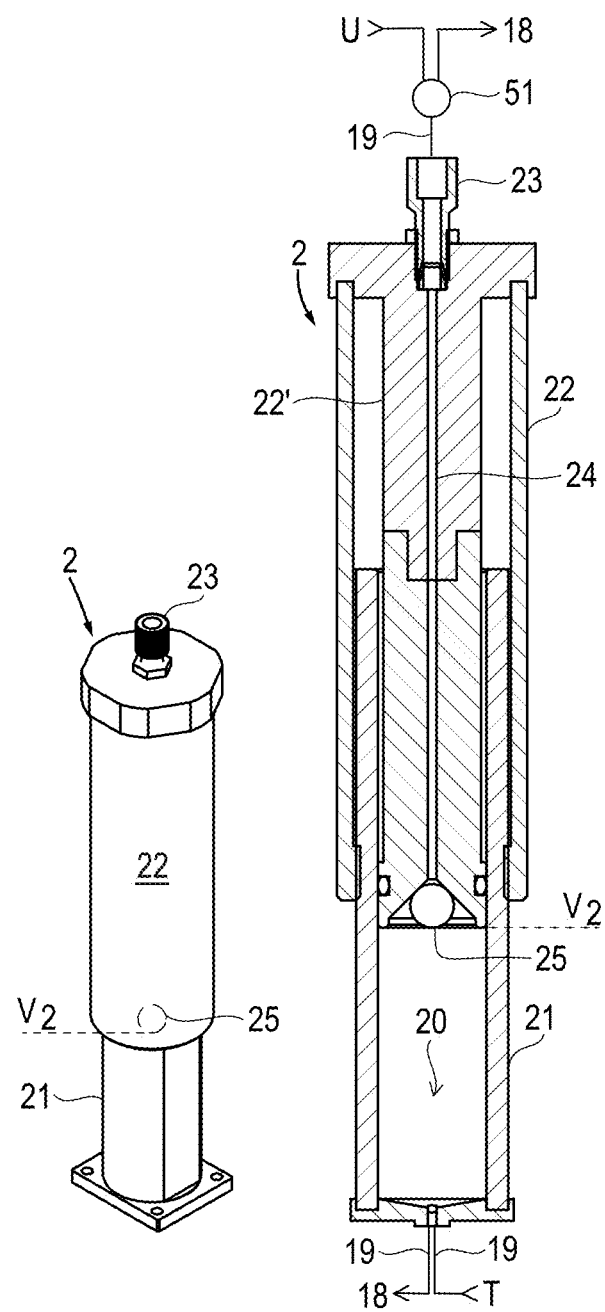
Fig. 9C  Fig. 9D  Fig. 9E  Fig. 9F

ARRANGEMENT FOR INTRODUCING DECONTAMINATION AGENT INTO AN ENCLOSURE

RELATED APPLICATIONS

This application is a U.S. National Phase Application under 35 U.S.C. 371 of International Application No. PCT/CH2019/000004 filed Feb. 21, 2019, which claims the benefit of European Patent Application No. 18405007.8 filed on Feb. 27, 2018. The disclosures of these applications are incorporated herein by reference in their entireties.

FIELD OF THE INVENTION

The invention relates to an arrangement for introducing a desired quantity of decontamination agent into a containment facility. Possible containment facilities are in particular isolators, for example for the pharmaceutical-chemical industry, sluices and safety workbenches, for example for microbiological tasks or tasks involving toxic substances. Moreover, the term includes all types of RABS (Restricted Access Barrier Systems) including mobile and stationary systems, such as means of transport and rooms for treating, isolating and/or diagnosing patients, as well as production rooms and laboratories. The arrangement includes a tank as a storage vessel for storing the decontamination agent in liquid form and also a metering apparatus having a spray nozzle that is directed into the containment facility so as to atomize the decontamination agent. A compressed air connection and a control unit are provided so as to operate the metering apparatus.

PRIOR ART

CH 689 178 A5 discloses an apparatus for the gaseous decontamination of clean rooms, said device having an evaporator unit, a vessel for storing a liquid decontamination agent, a feeder device and a control unit for the process sequence. Whereas the evaporator unit is arranged inside the clean room, a hose line extends from the storage vessel that is positioned outside the clean room that is to be decontaminated.

CH 699 032 B1 discloses a method for the decontamination of a clean room and of treatment articles that may be brought temporarily into said clean room. A decontamination agent that is in liquid form in the normal state is supplied from a storage vessel by way of a feed line to a heatable evaporator. The vaporous decontamination agent that is produced in the evaporator is introduced by way of a feed line merely by means of adiabatic expansion directly into the clean room in order to precipitate as a condensate in the clean room and in the event that treatment articles have been brought into the clean room to precipitate on said treatment articles. After a defined reaction time, the precipitated condensate is removed from the clean room in a flushing phase.

The subject of WO 2008/116 341 A2 is a decontamination arrangement for a clean room within an isolator or a sluice and for treatment articles that may be brought temporarily into the clean room. A storage vessel is used to provide a decontamination agent that is in liquid form in the normal state. Moreover, an evaporator apparatus is provided that comprises a heatable evaporator that comprises an evaporator cell. A first feed line leads from the storage vessel to the evaporator cell. A feeder assembly is arranged in the first feed line so as to transport the decontamination agent into the evaporator cell. A second feed line leads from a compressed air unit into the evaporator cell. The vaporized decontamination agent that is produced in the evaporator cell is introduced into the clean room by means of a flow connection that extends from the evaporate cell. The flow connection is formed by a nozzle, which is connected to the evaporator cell, with its inner hollow chamber and the junction that continues therefrom. The nozzle comprises a head, from which the junction flows outwards, and has a shaft that protrudes through the floor of the clean room as far as the evaporator cell.

WO 2013/003 967 A1 proposes an apparatus for the decontamination of a containment facility and/or of treatment articles that may be brought temporarily into said containment facility, said apparatus having a reservoir for storing a decontamination agent that is liquid in the normal state. Moreover, the apparatus comprises an atomizer that is influenced by a compressed air source so as to convert the decontamination agent into an aerosol. The apparatus has at least one outlet that is provided for introducing the aerosol, which is produced in the apparatus, directly into the containment facility. The reservoir and the atomizer are an integral component of the apparatus that may be installed as a whole on or in the containment facility. The reservoir is filled with decontamination agent in the factory or may be filled prior to use by the user. The entire apparatus or at least the reservoir is configured as a disposable item. The atomizer is a Venturi nozzle into which a primary duct flows and said primary duct leads to the reservoir. A secondary duct flows into the atomizer and has a connection to the compressed air source. The fill quantity in the reservoir is determined for a defined volume of a containment facility.

US 2011/0 266 376 A1 discusses an arrangement for introducing a desired quantity of decontamination agent into a containment facility. A tank has the function of a storage vessel for storing the decontamination agent in liquid form. Moreover, the arrangement comprises a metering apparatus having a spray nozzle that is directed into the containment facility so as to atomize the decontamination agent. The metering apparatus comprises a metering container that comprises a storage chamber that has a defined volume for receiving an individual portion of decontamination agent. A compressed air connection and a control unit are used to operate the metering apparatus.

EP 2 839 845 A1 relates to an apparatus that uses nitrogen oxide to sterilize articles that have been brought into a containment facility. The sterilization liquid is stored in a container and is supplied by way of a through-flow counter or a metering pump in a calculated required quantity to a spray nozzle that flows into the containment facility for the purpose of acting on the article.

Finally, EP 2 692 848 A1 discusses an apparatus for introducing a mist of decontamination agent into a containment facility that comprises a storage vessel from which a defined liquid volume is transported into a bottle by means of a controlled pump. A level sensor on the bottle signals that the pump is to be switched off if the set liquid level is realized. The decontamination agent is drawn off by means of suction from the bottle and supplied to an atomizer that flows into the containment facility. The apparatus with the components and the manner in which said components are positioned with respect to one another renders it possible to produce a fine mist of decontamination agent without having to use a heater and an ultra-sound atomizer, and simultaneously it is prevented that larger liquid drops are sprayed into the containment facility.

OBJECT OF THE INVENTION

In the case of the hitherto known structural designs that use a metering apparatus for introducing the decontamination agent into a containment facility, the heated evaporators are often encumbered with problems. In order to introduce a precise as possible metered quantity into the containment facility, it is necessary to use a cost-intensive measuring apparatus, at least one set of scales that require the corresponding amount of space and line connections. A further disadvantage of many of the devices provided for the mentioned purpose is the considerable amount of time required to perform a decontamination process.

In relation to the hitherto known prior art, the object of the invention is based on an innovative arrangement for introducing a desired quantity of decontamination agent into a containment facility. An overall cost-effective solution is to be realized with respect to the outlay relating to the components used, the amount of space required, the accuracy of the metered quantity, the level of safety, the wide range of possible applications and time saved when performing the decontamination processes.

OVERVIEW OF THE INVENTION

The arrangement is proposed for introducing a desired quantity of decontamination agent into a containment facility. The arrangement includes a tank as a storage vessel for storing the decontamination agent in liquid form and also a metering apparatus having a spray nozzle that is directed into the containment facility so as to atomize the decontamination agent. A compressed air connection and a control unit are provided so as to operate the metering apparatus. The metering apparatus has a metering container that comprises a storage chamber that has a defined volume for receiving an individual portion of decontamination agent. The storage chamber is used to sequentially receive a number of portions of decontamination agent from the tank, while the portion that is respectively held in the storage chamber is provided so as to be introduced by means of the spray nozzle into the containment facility prior to receiving a subsequent portion. The number of portions for realizing the desired quantity of required decontamination agent may be selected between 1 and a whole number multiple of 1.

Particular embodiments of the invention are defined below: the storage chamber is configured with a fixed or adjustable size and provided as a separate container, a cylinder, a recess in the metering container or as an extended or drawn tube length. The storage chamber has a volume in the range of 1 $cm^3$ to 50 $cm^3$, preferably in the range of 1 $cm^3$ to 5 $cm^3$.

For example, a standpipe, a piston or an electrical probe, which may be inserted into the storage chamber and whose position may be adjusted, or a hose winding or tubing winding with a specific inner cross-section and length of winding are used in order to be able to adjust the size of the portion of decontamination agent that may be held in the storage chamber The compressed air connection is used to fill the storage chamber with decontamination agent from the tank and to operate the spray nozzle based on the Venturi principle. The metering apparatus comprises a feeder device for filling the storage chamber with decontamination agent from the tank. A fill level sensor, a closure element or an adjustable standpipe, an adjustable piston or an adjustable electrical probe are used so as to signal that a complete portion of decontamination agent has been supplied into the storage chamber and that the supply from the tank is to be terminated. The closure element is provided as a floatation body that is arranged in the storage chamber or as a semipermeable membrane. The adjustable electrical probe cooperates with a fixed electrical contact and they are both covered by the decontamination agent when a complete portion of decontamination agent has been supplied.

It is possible to program into the control unit the time sequence with the start, the process flow and the termination of the procedure of introducing the desired quantity of decontamination agent into the containment facility and the desired quantity by virtue of determining the number of portions. It is also possible to program that, after the process of introducing the desired quantity of decontamination agent into the containment facility has been terminated, any decontamination agent remaining in the metering apparatus is returned to the tank.

In order to introduce the desired quantity of decontamination agent into the containment facility, the following are provided for controlling the process flow and the metered quantity:

a) a first category of control elements in the form of 3-way valves which are influenced by the control unit by way of control lines and are installed in substance lines that convey decontamination agent or ambient air;

b) a second category of control elements in the form of stop valves which are influenced by the control unit by way of control lines and are installed in substance lines that convey decontamination agent or ambient air; and c) a third category of control elements in the form of restrictor valves, preferably adjustable, which are installed in substance lines that convey decontamination agent or compressed air.

The compressed air and ambient air that are supplied into the arrangement flow through cleaning filters.

The metering apparatus is designed as a compact assembly and may be installed in close proximity to the containment facility in order to realize a minimal length of the substance line from the storage chamber to the spray nozzle and consequently to realize a minimal transportation time for the decontamination agent that is supplied in portions from the storage chamber in the spray nozzle.

The tank, the source for the compressed air and the control unit are located outside the metering apparatus. In so doing, the metering apparatus is controlled by way of the central control unit that is already provided for the containment facility. Alternatively, it is also possible to provide a separate control unit that is integrated into the metering apparatus.

Defined on the metering apparatus in accordance with a first variant of the arrangement are:

a) a first connection site by means of which a substance line originating from the tank leads into the metering apparatus, wherein a substance line that forms a feed line from the ambient air flows into the tank; and b) a second connection site, a third connection site and a fourth connection site, by means of which respectively a substance line that originates from the compressed air connection leads into the metering apparatus.

Moreover, the metering apparatus comprises:

a) a first control element and the substance line that continues from the first connection site leads to said first control element and said first control element is connected by way of a control line to the control unit;

b) a fifth control element and the substance line that continues from the second connection site leads to said fifth control element and said fifth control element is connected by way of a control line to the control unit;

c) a sixth control element and the substance line that continues from the fourth connection site leads to said sixth control element and said sixth control element is connected by way of a control line to the control unit.

A fourth control element that is connected by way of a control line to the control unit is installed in the substance line that conveys compressed air to the third connection site.

A substance line continues from the first control element to the metering container that has the storage chamber arranged therein, and a further substance line extends from the first control element to the spray nozzle. A substance line continues from the fifth control element and continues to a feeder device that flows into the ambient air and is preferably in the form of a Venturi nozzle. A substance line extends from the third connection site to the spray nozzle. A substance line continues from the sixth control element and flows above a fill level sensor into the substance line that leads onwards to the first safety element.

A substance line extends from the storage chamber by way of a fill level sensor, which is connected via a control line to the control unit, onwards to a first safety element and from there to the feeder device. An eighth control element, preferably in the form of an adjustable restrictor valve, is installed in the substance line between the fifth control element and the feeder device. A ninth control element, preferably in the form of a restrictor valve, is installed in the substance line between the sixth control element and its junction into the substance line that leads onwards to the first safety element.

An empty status sensor that is connected via a control line to the control unit is installed in the substance line between the first control element and the metering container. A second safety element is provided in the substance line between the first safety element and the feeder device, wherein the two safety elements are preferably configured as semi-permeable membranes. A seventh control element, preferably in the form of an adjustable restrictor valve, is installed in the other substance line between the first control element and the spray nozzle.

BRIEF DESCRIPTION OF THE ATTACHED DRAWINGS

Figure 1B:
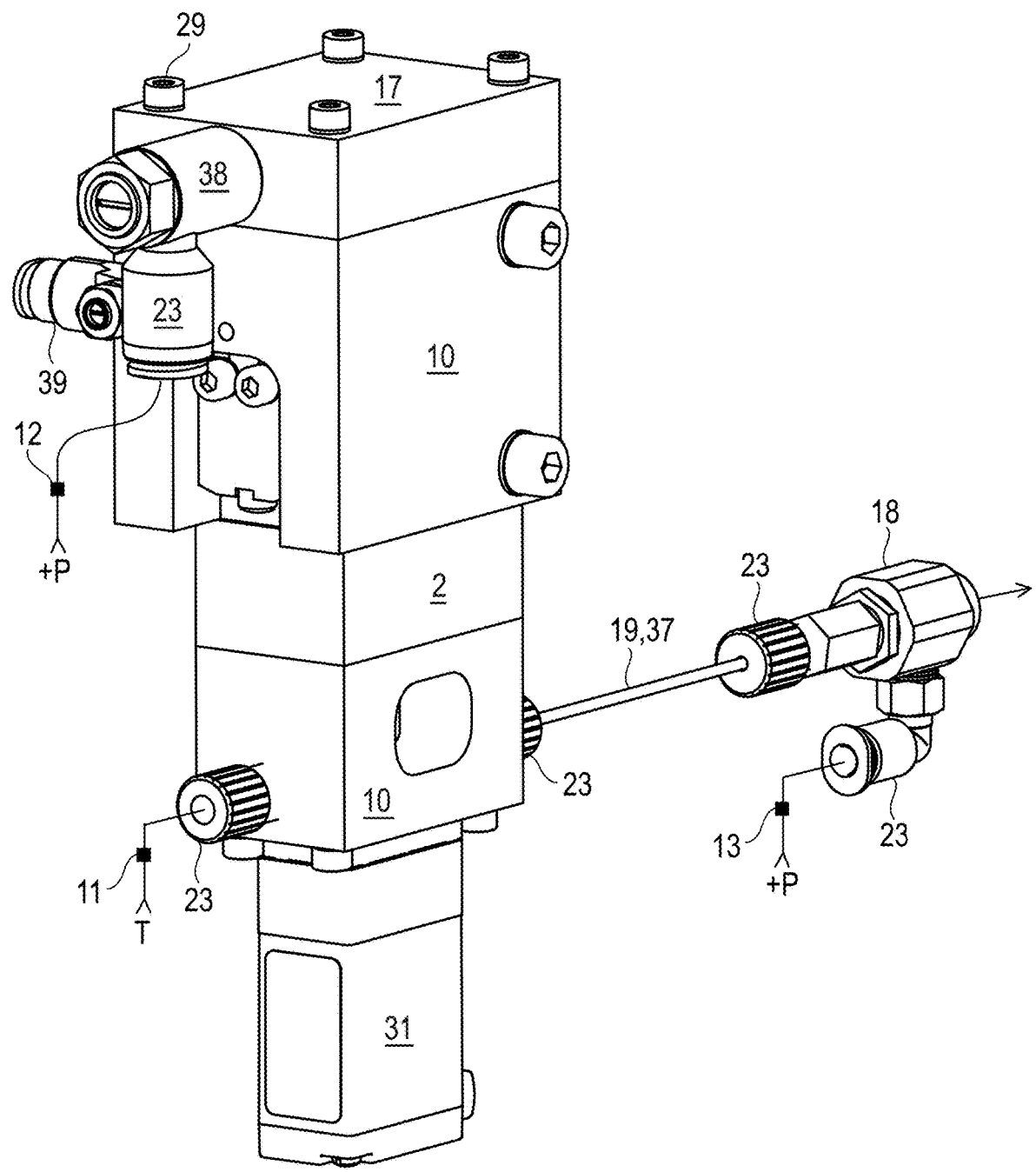
Figure 1D:
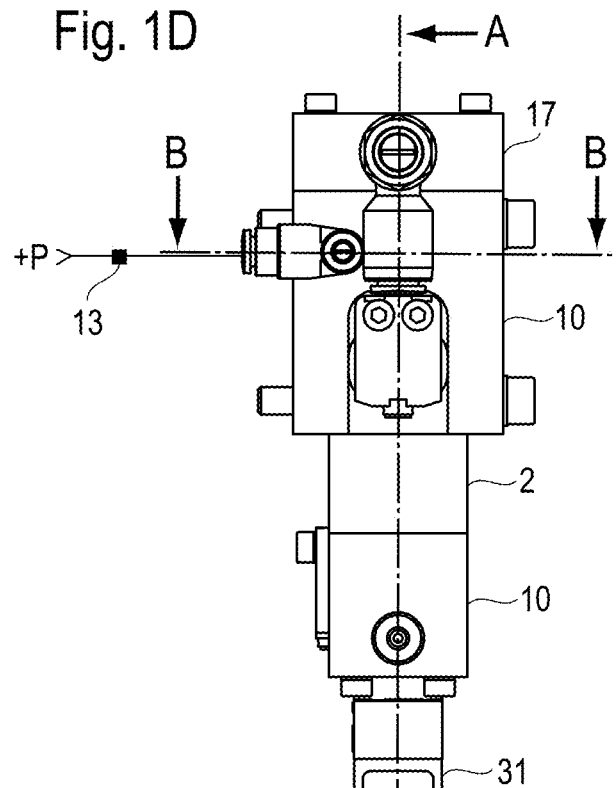
Figure 1C:
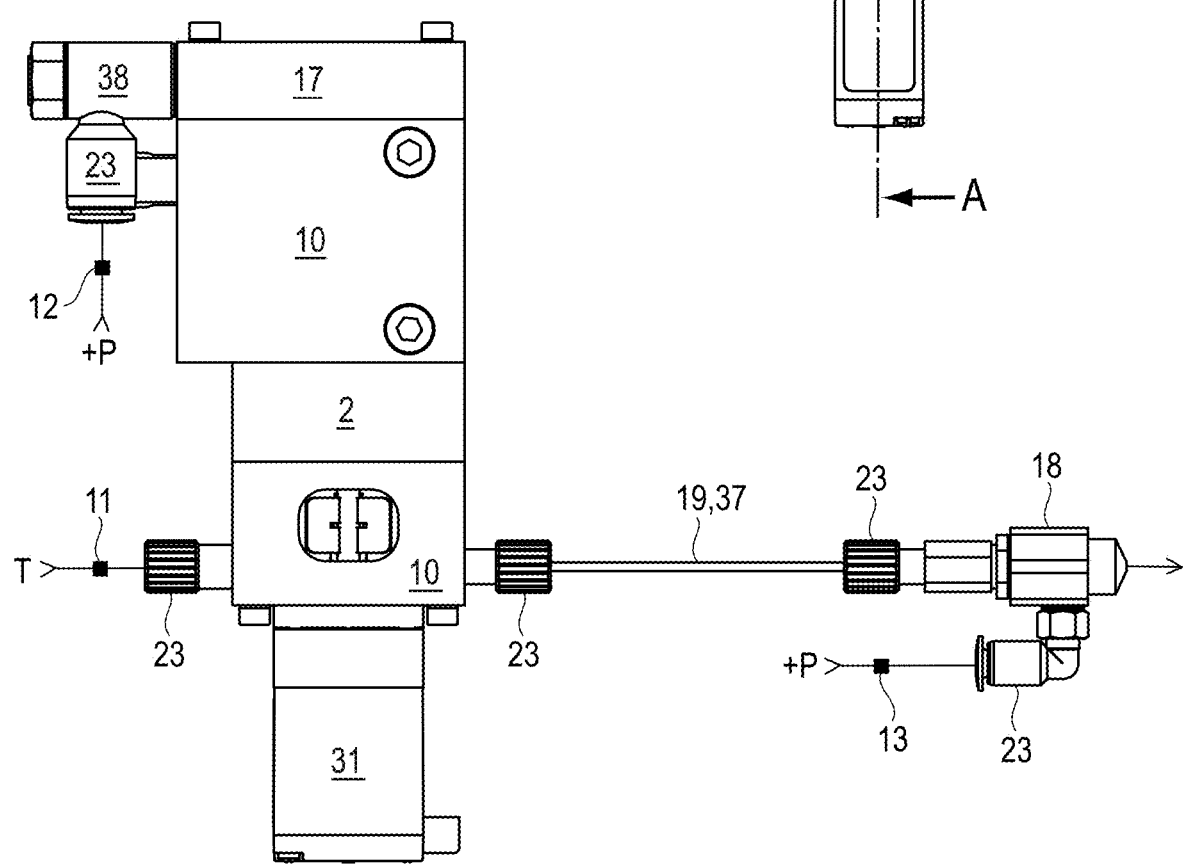
Figure 1E:
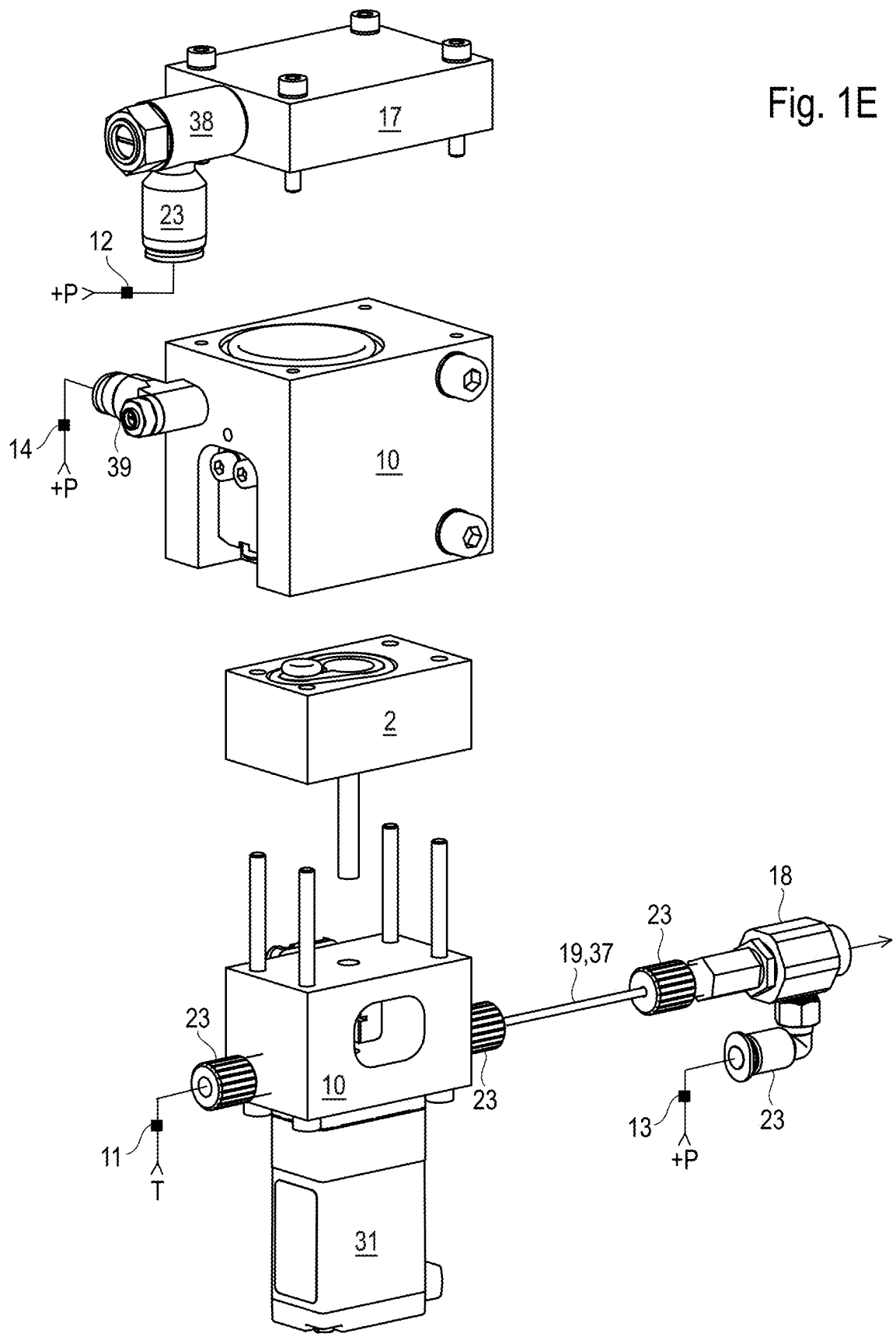
Figure 1F:
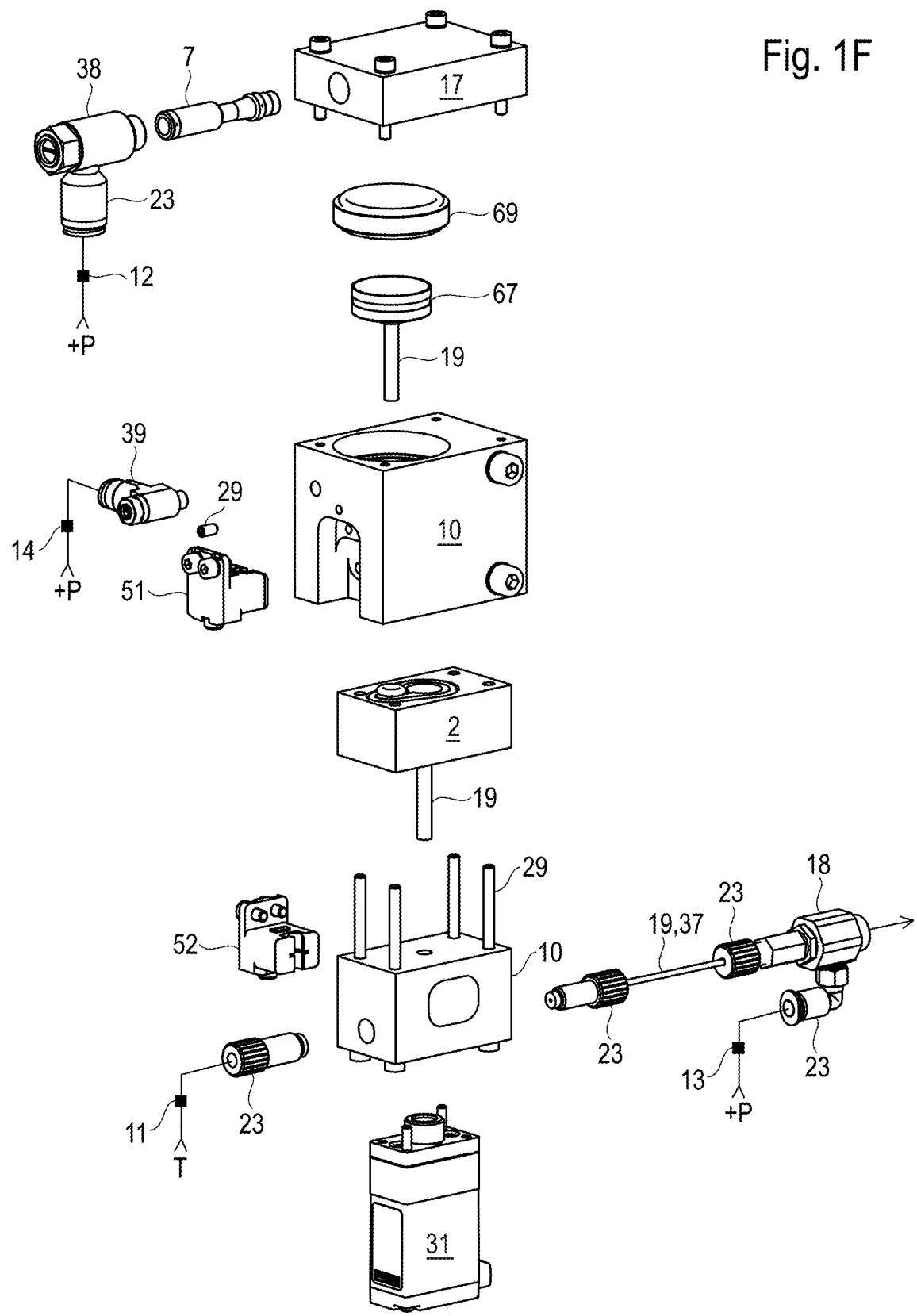
Figure 1G:
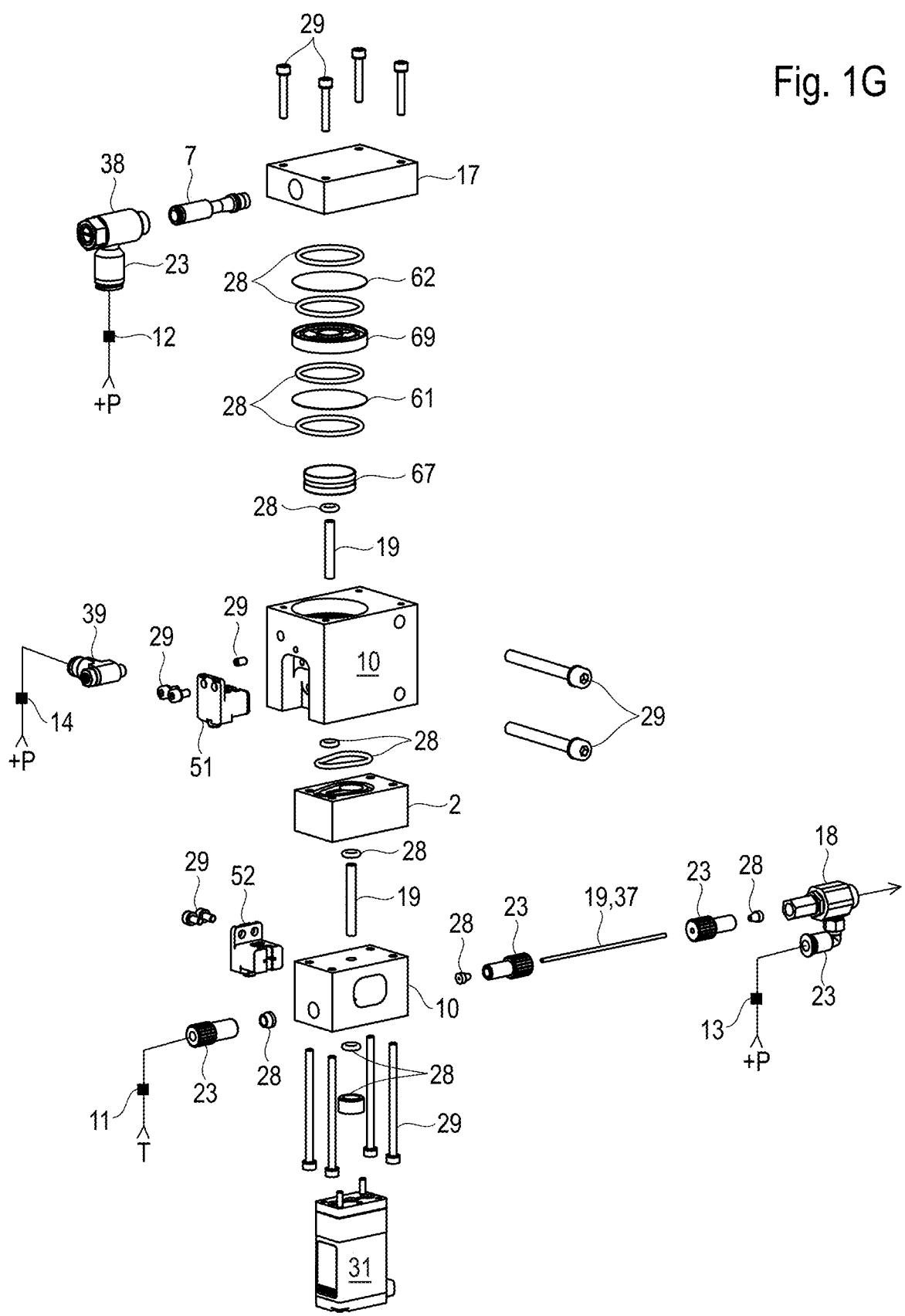
Figure 1H:
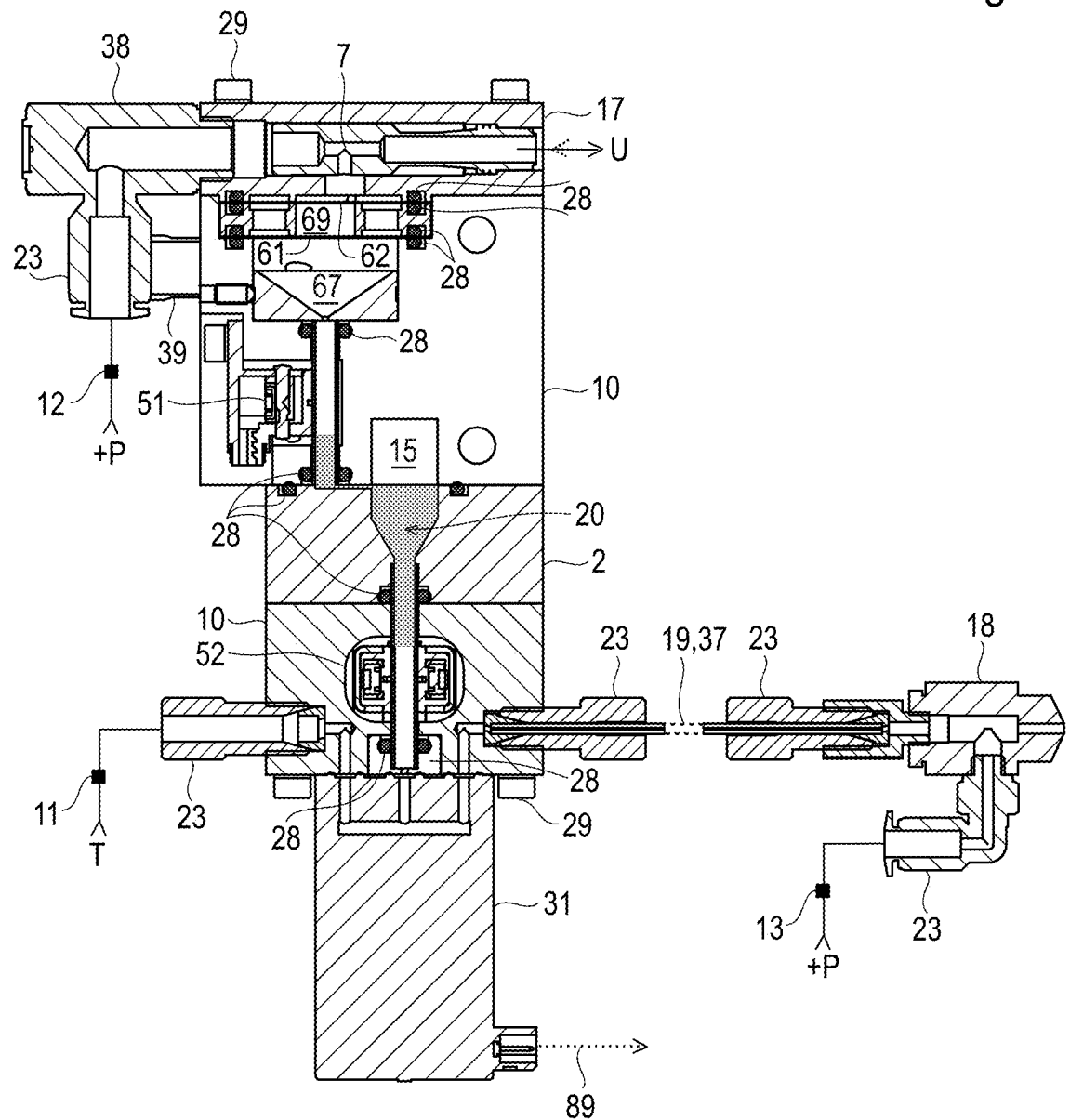
Figure 1J:
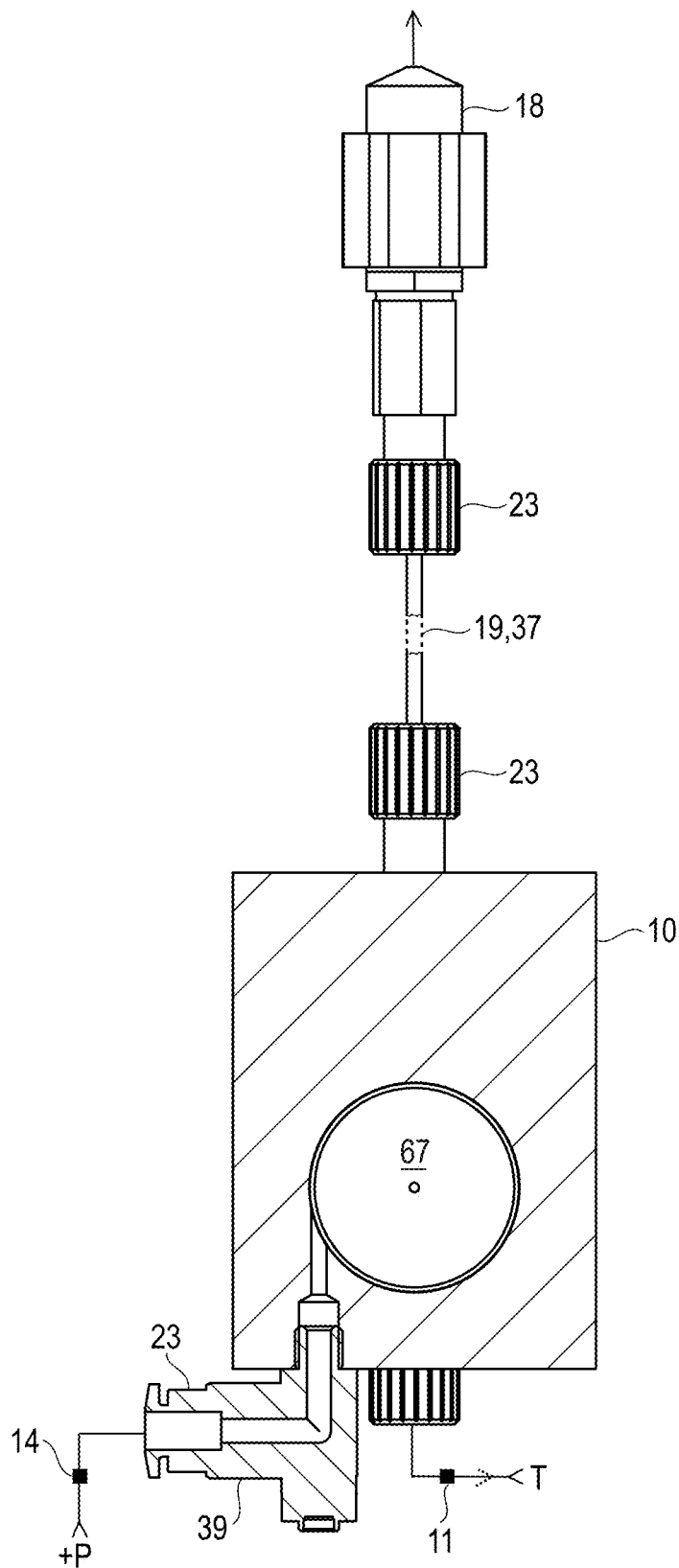
Figure 2A:
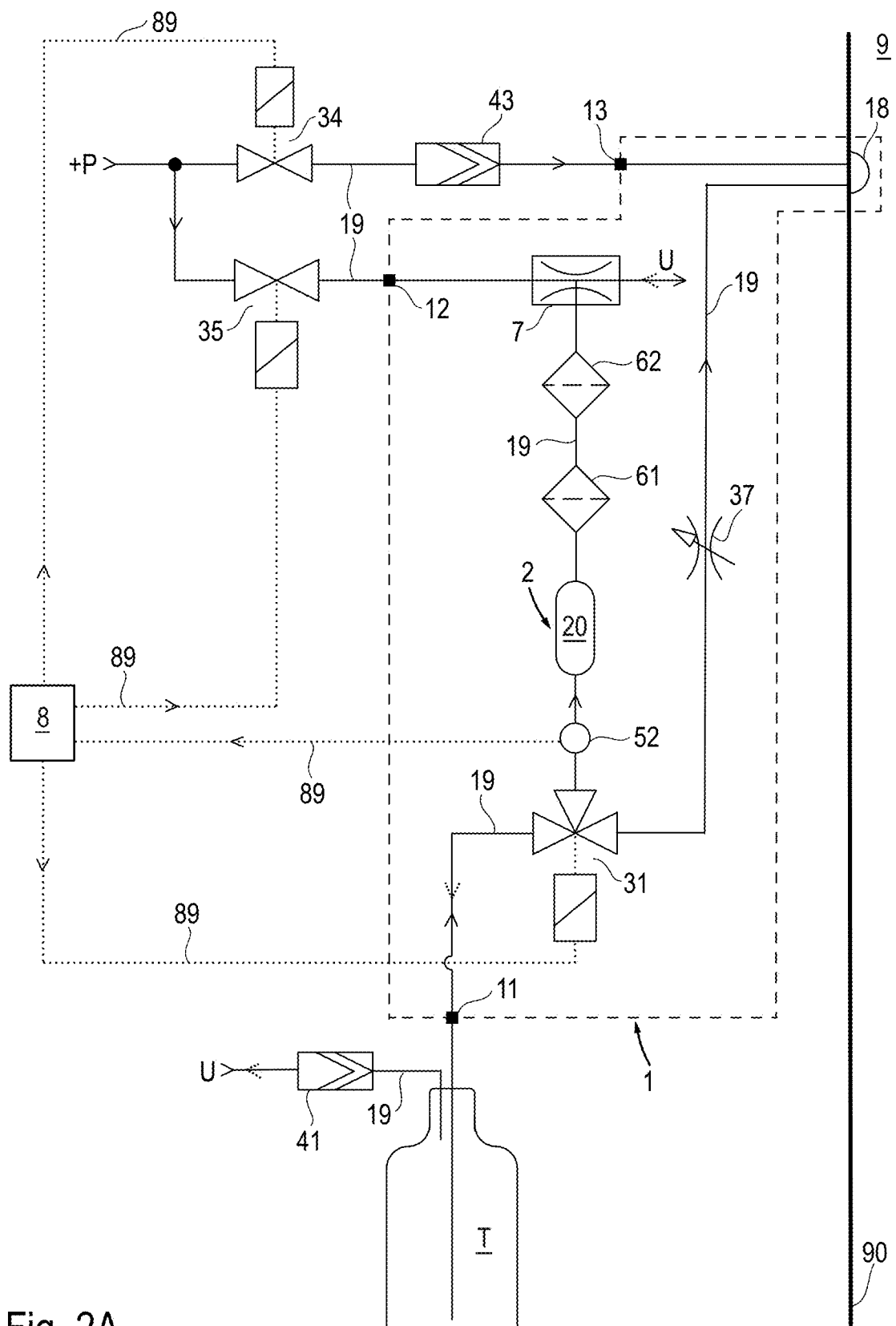
Figure 2B:
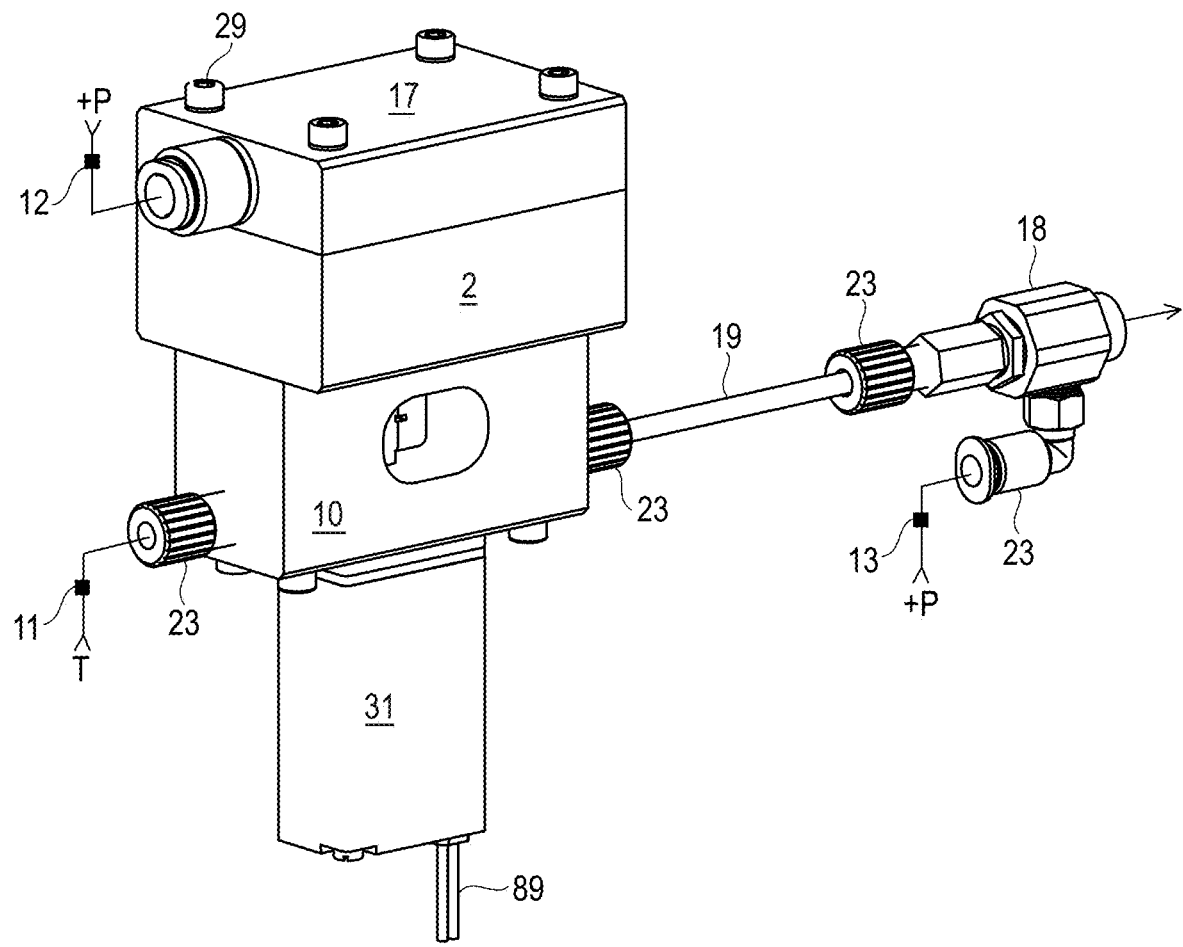
Figure 2C:
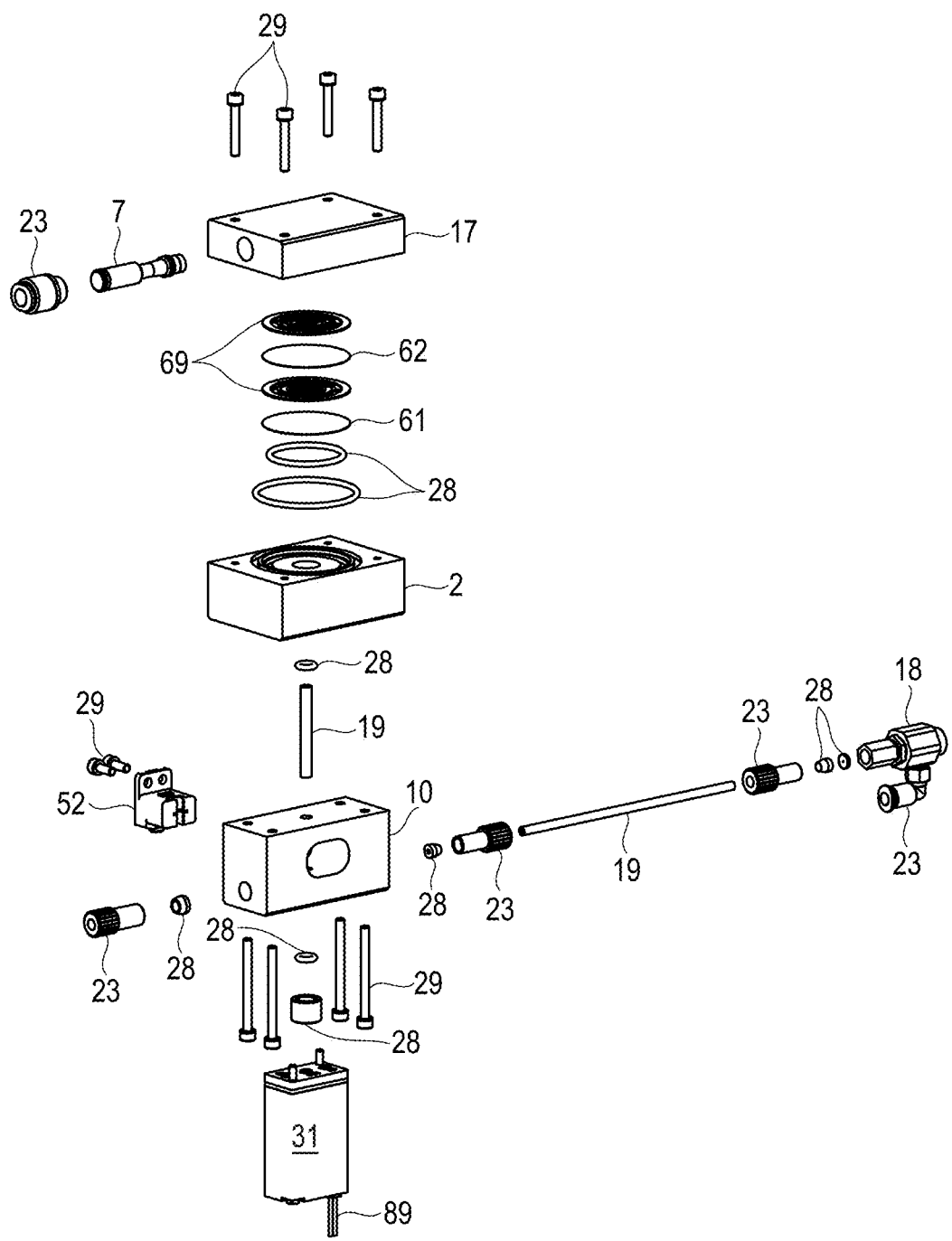
Figure 3A:
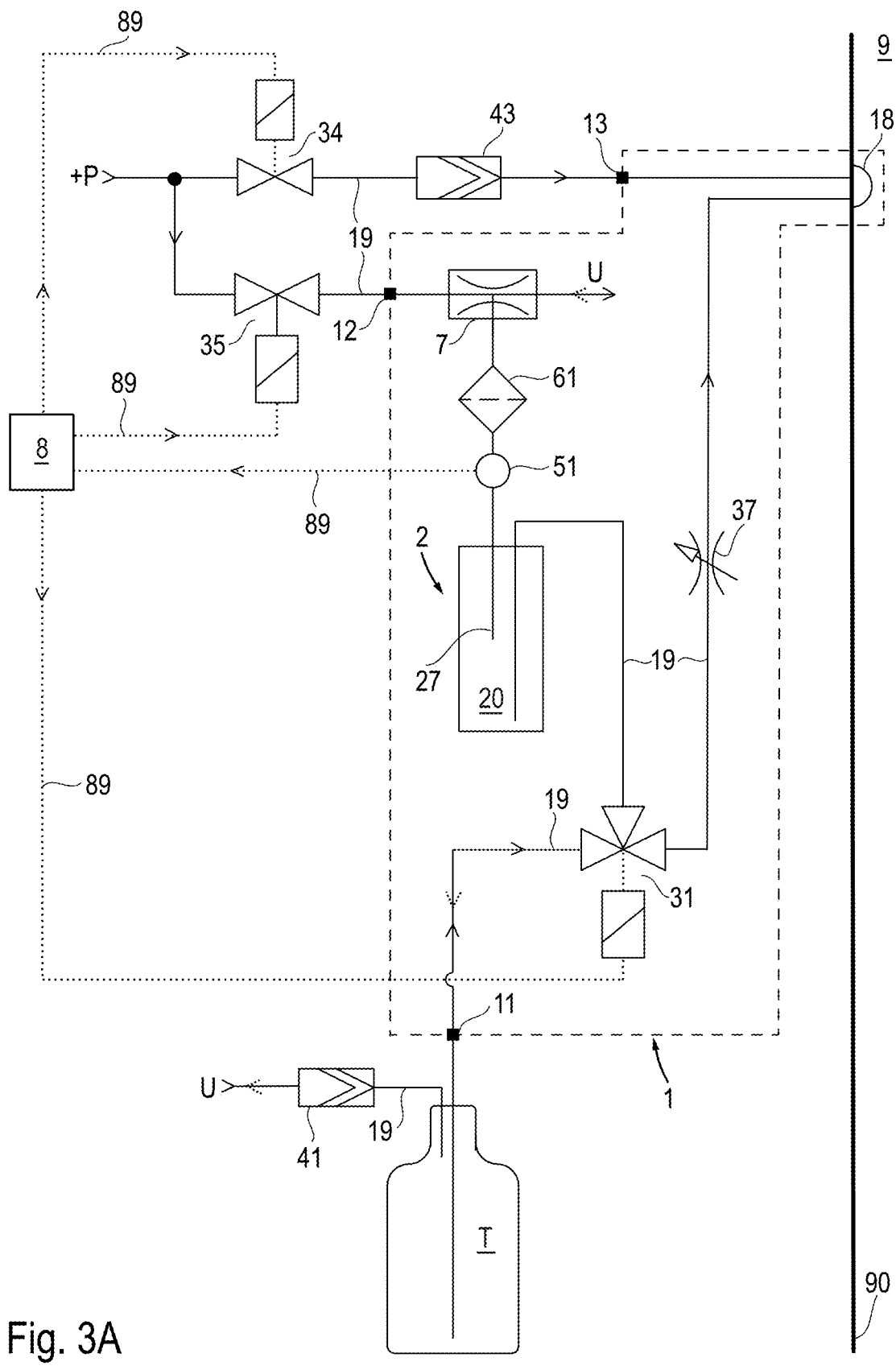
Figure 3B:
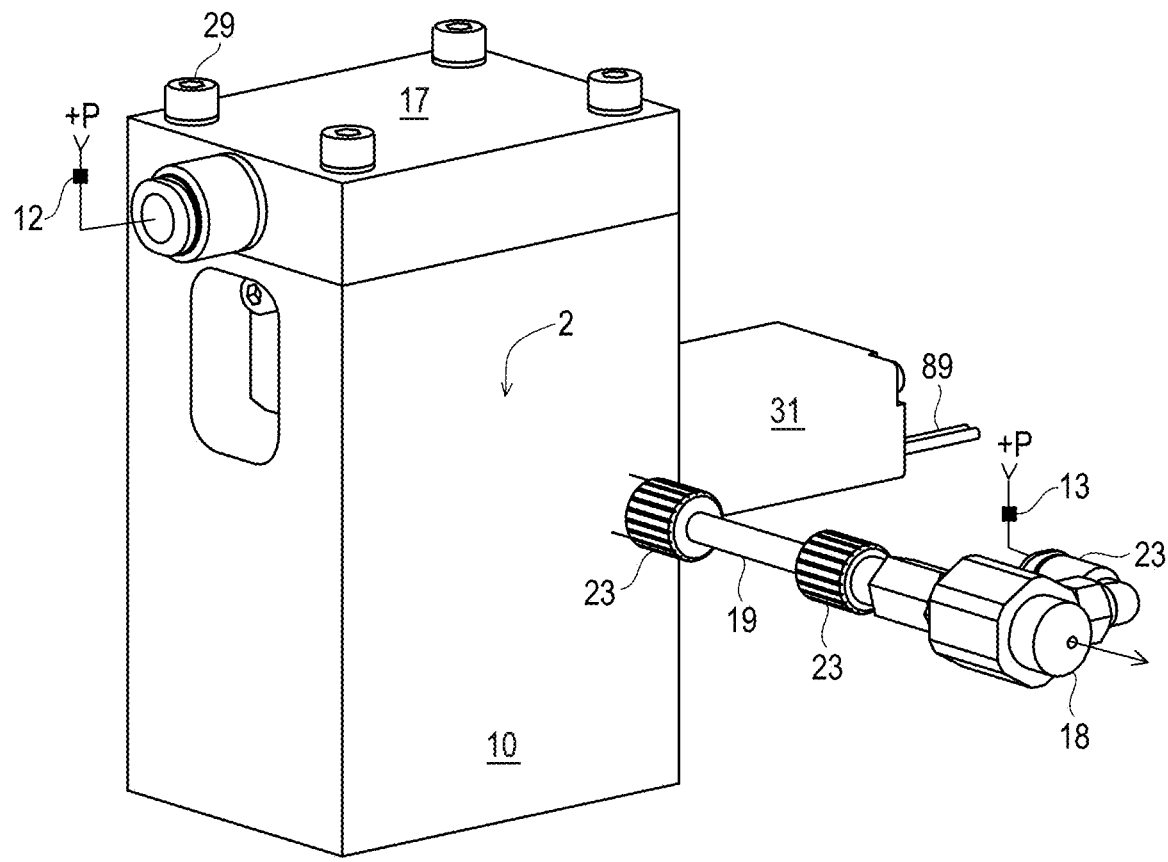
Figure 3C:
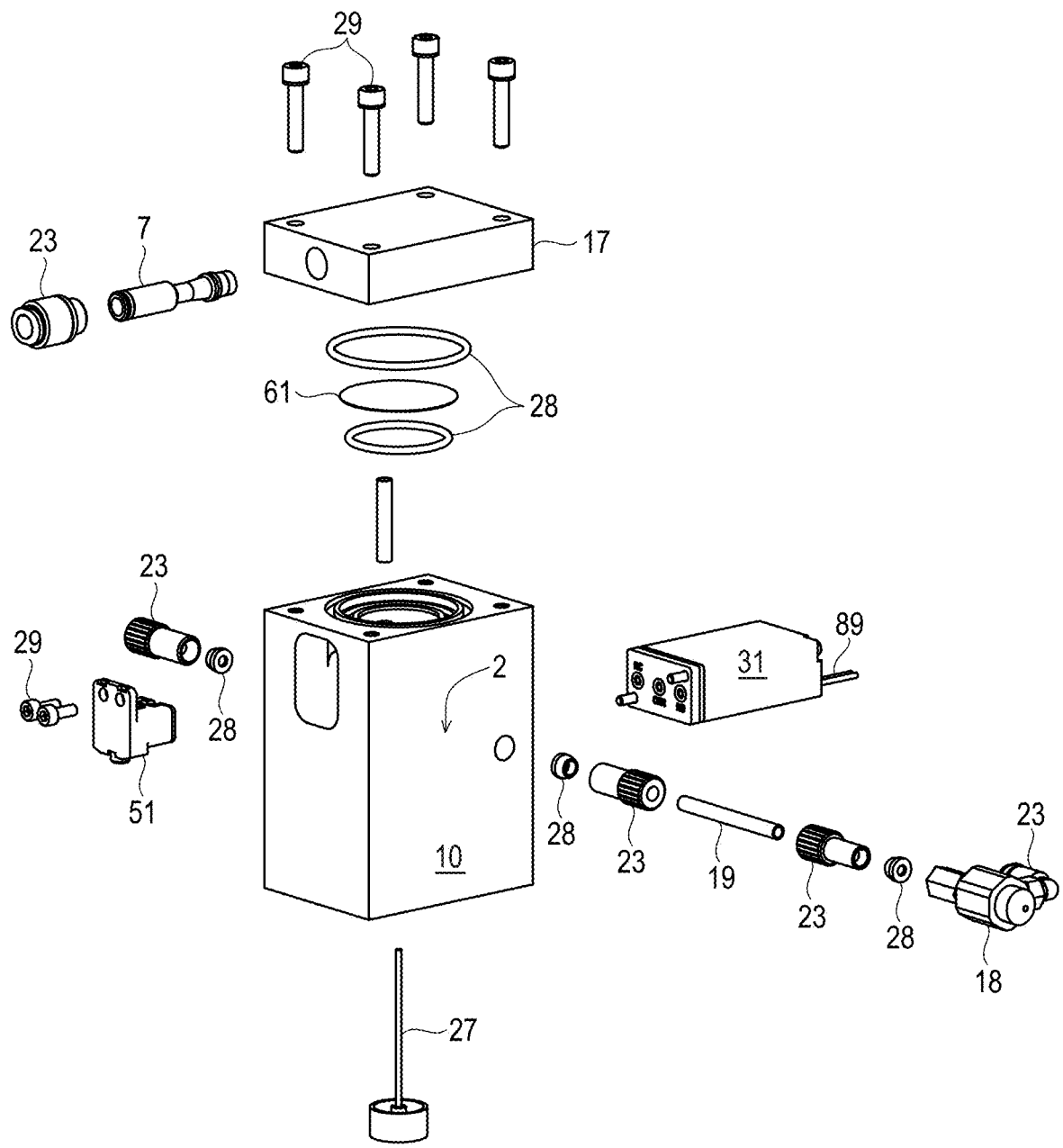
Figure 4A:
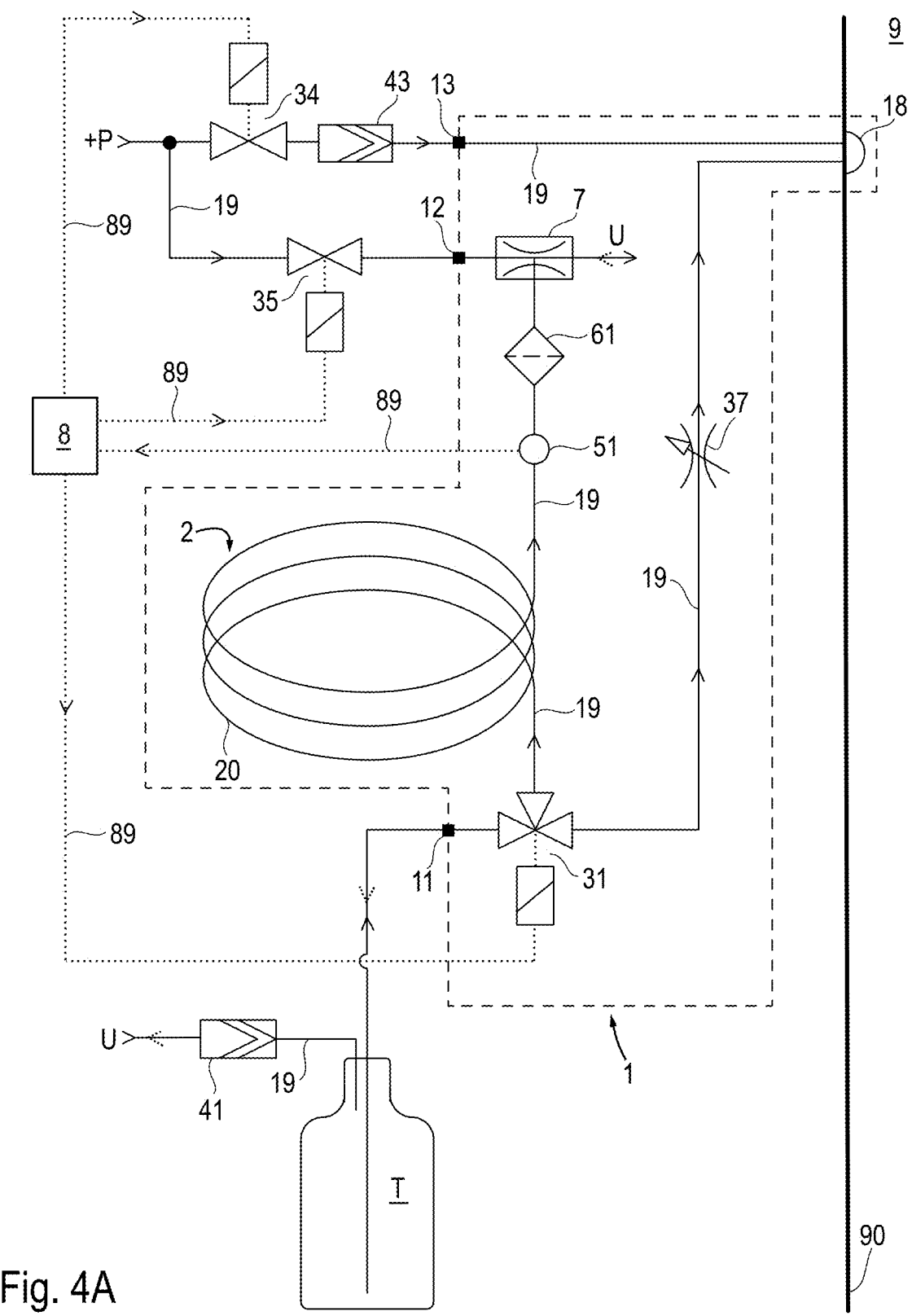
Figure 4B:
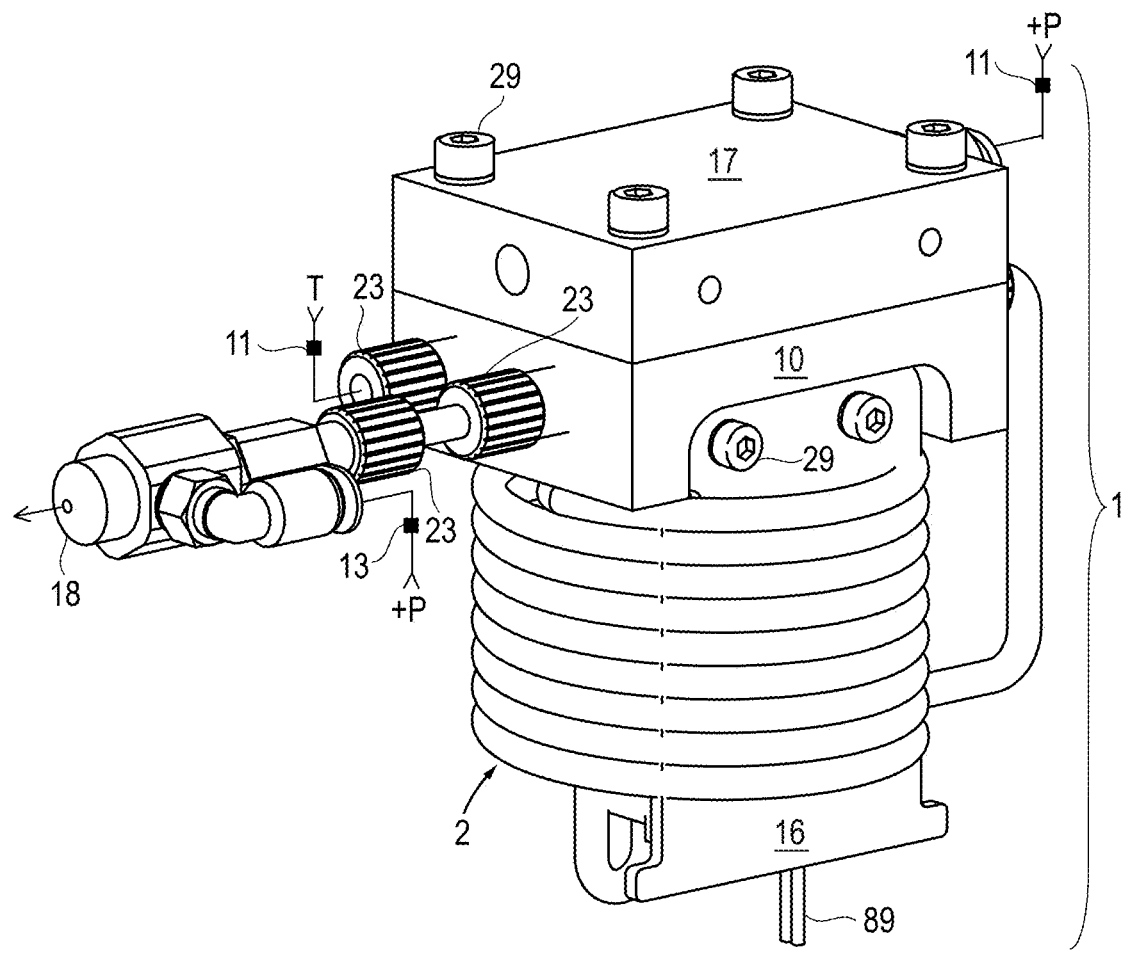
Figure 4C:
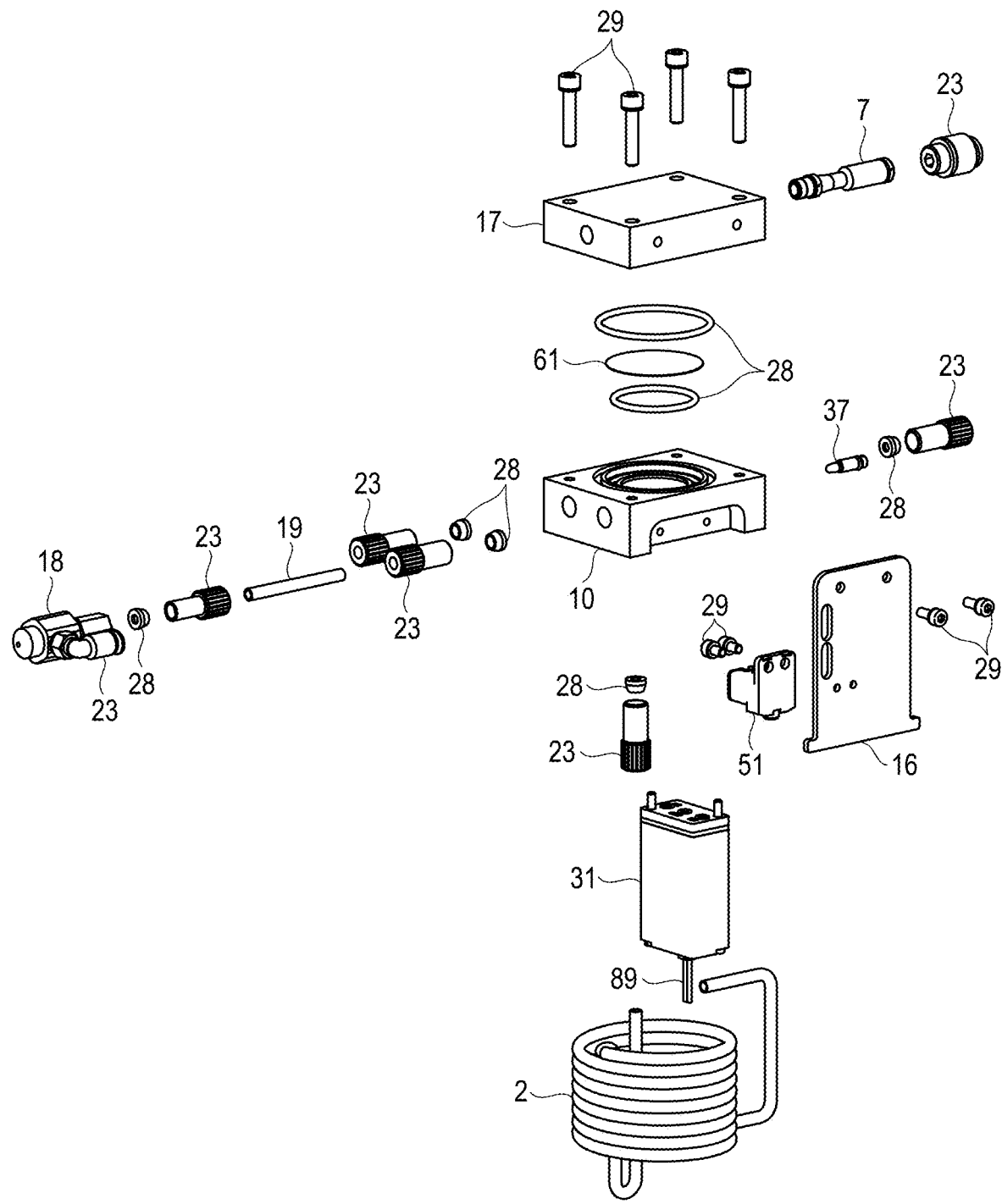
Figure 5:
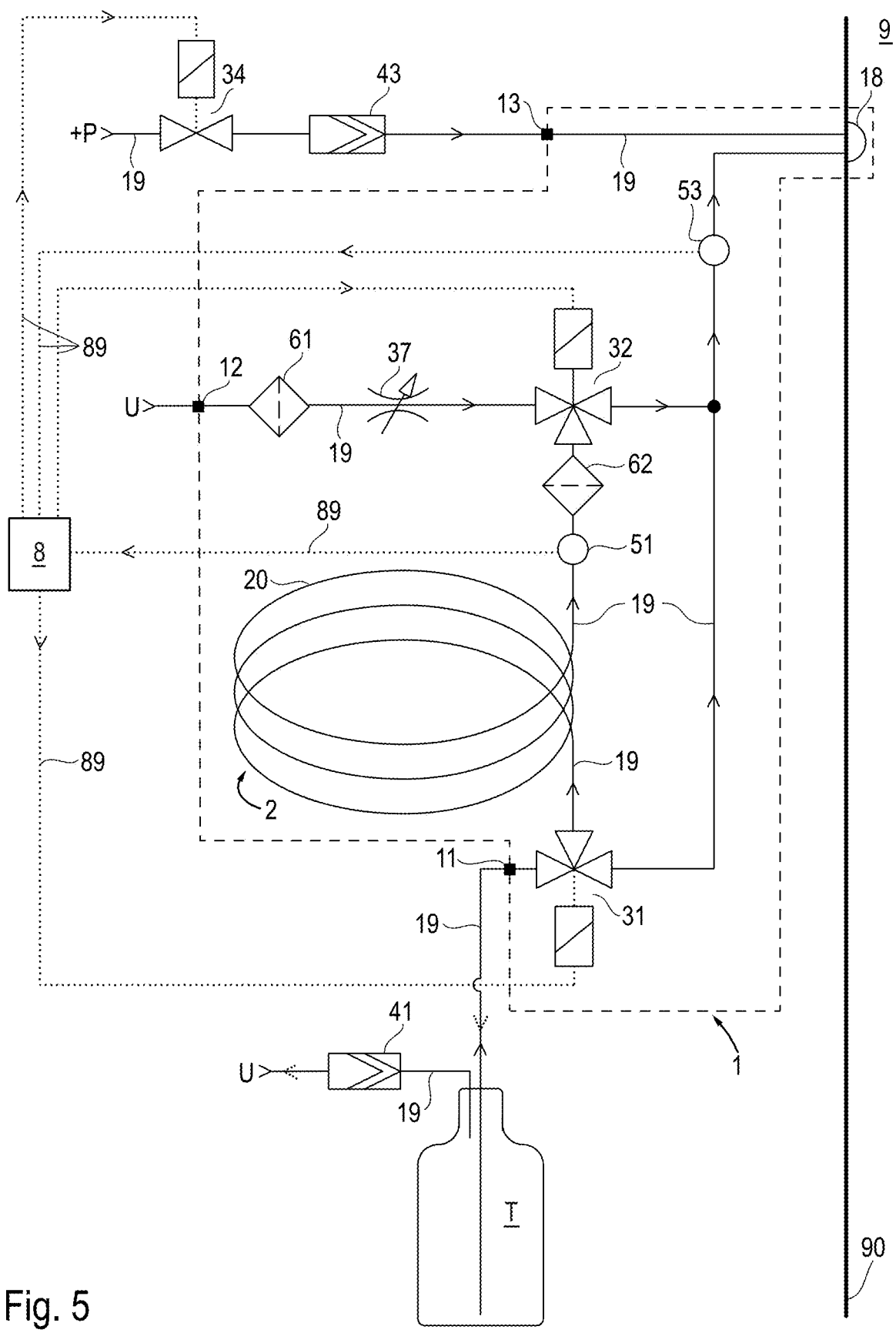
Figure 6:
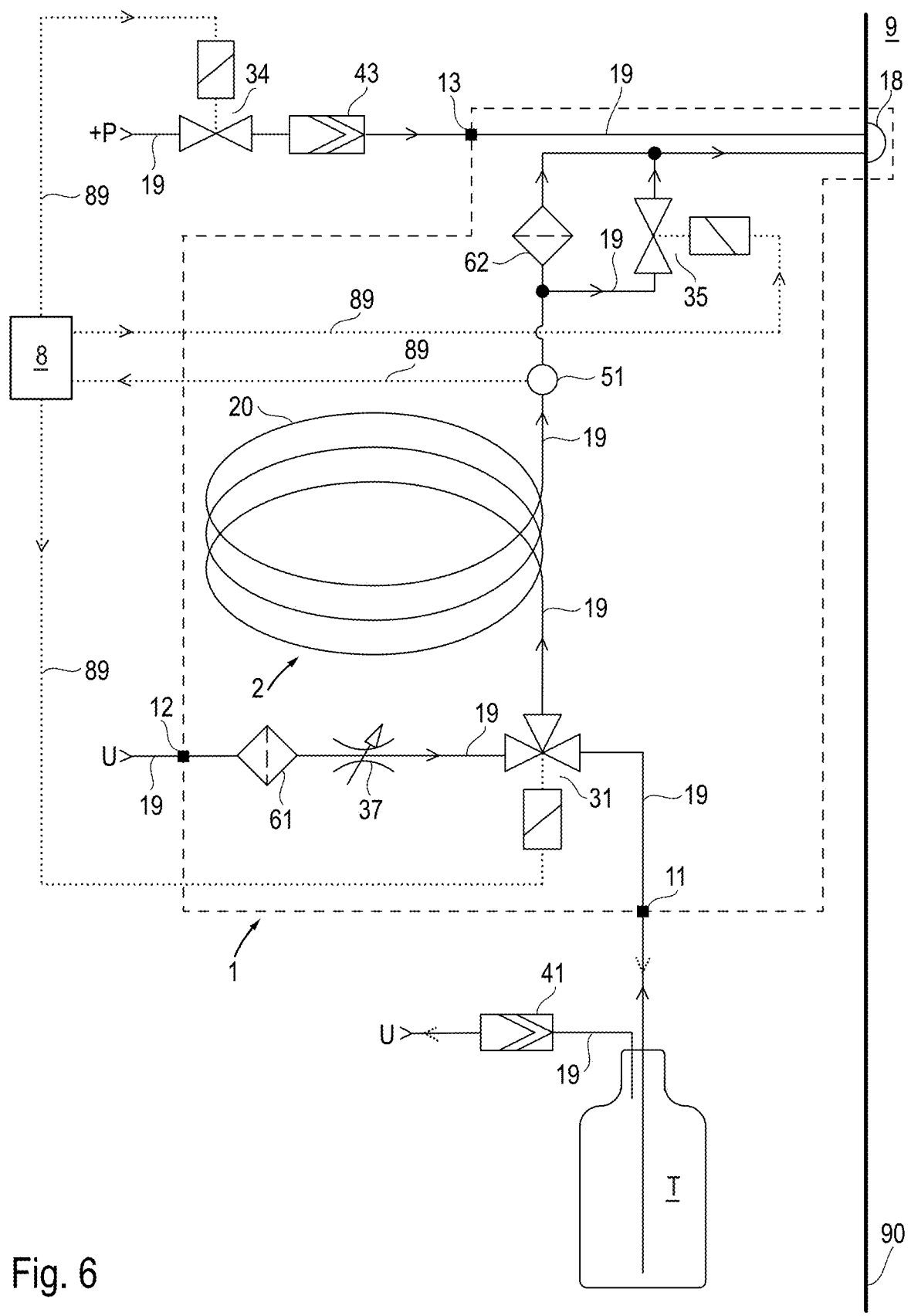
Figure 7:
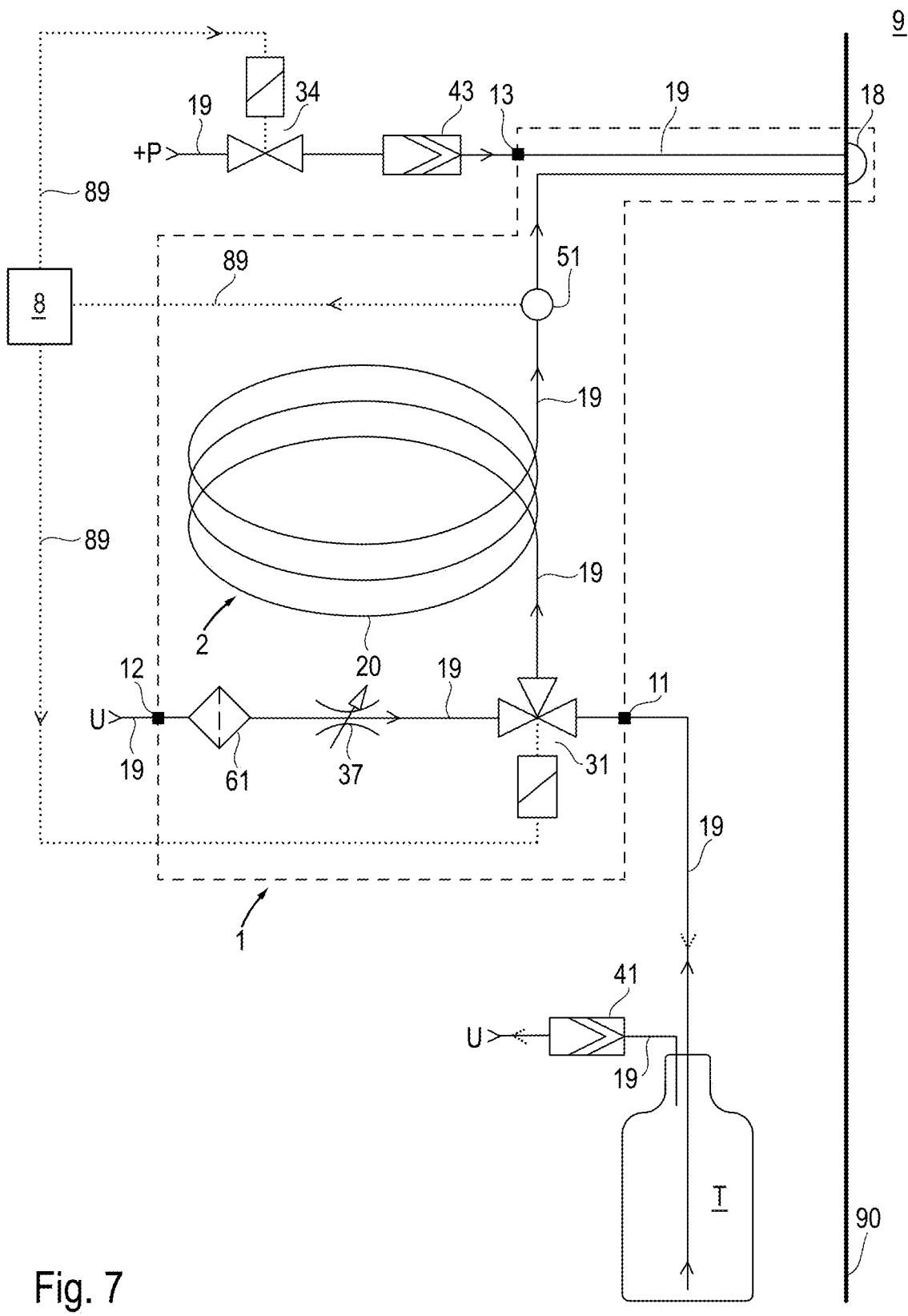
Figure 8:
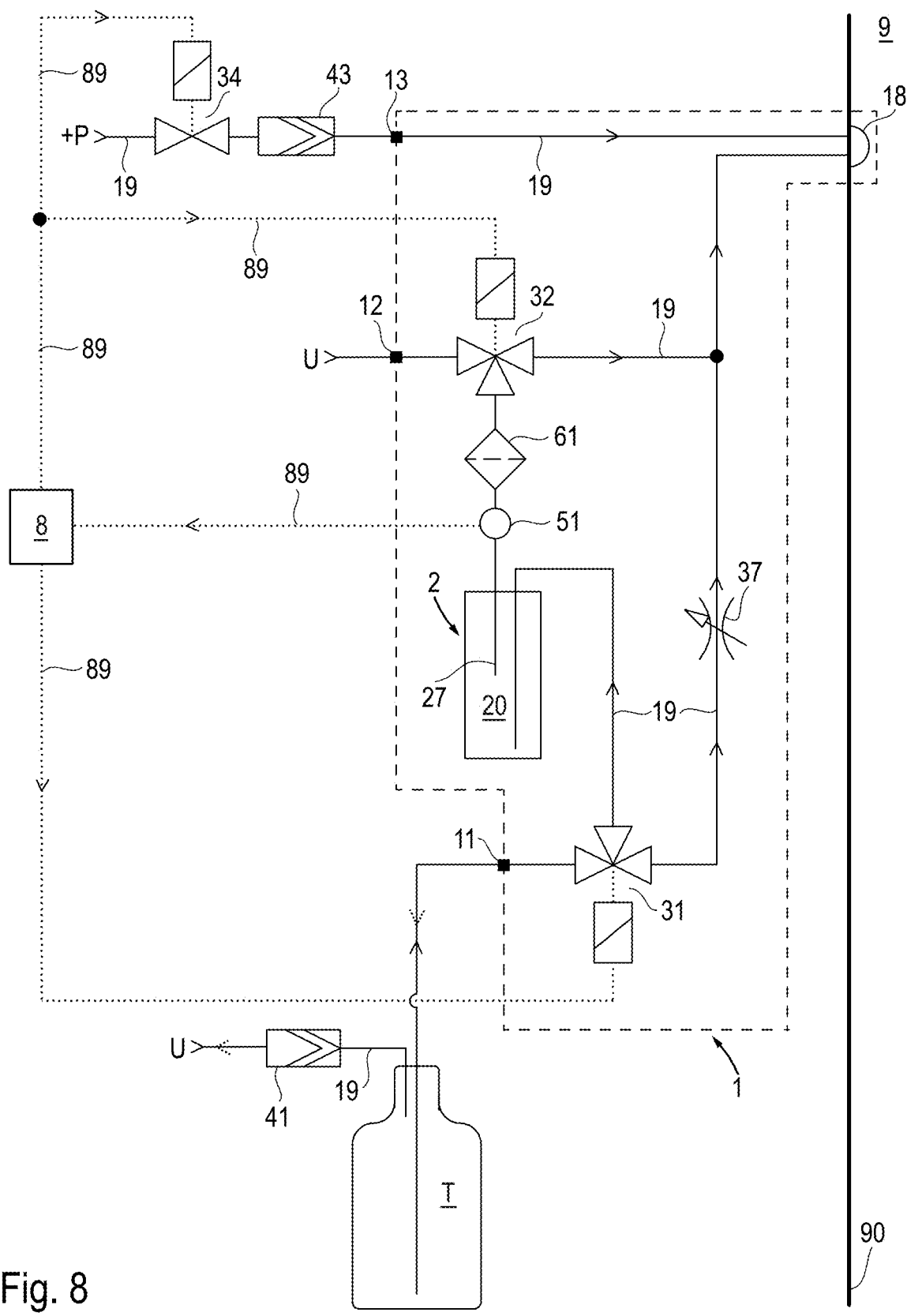
Figure 9A:
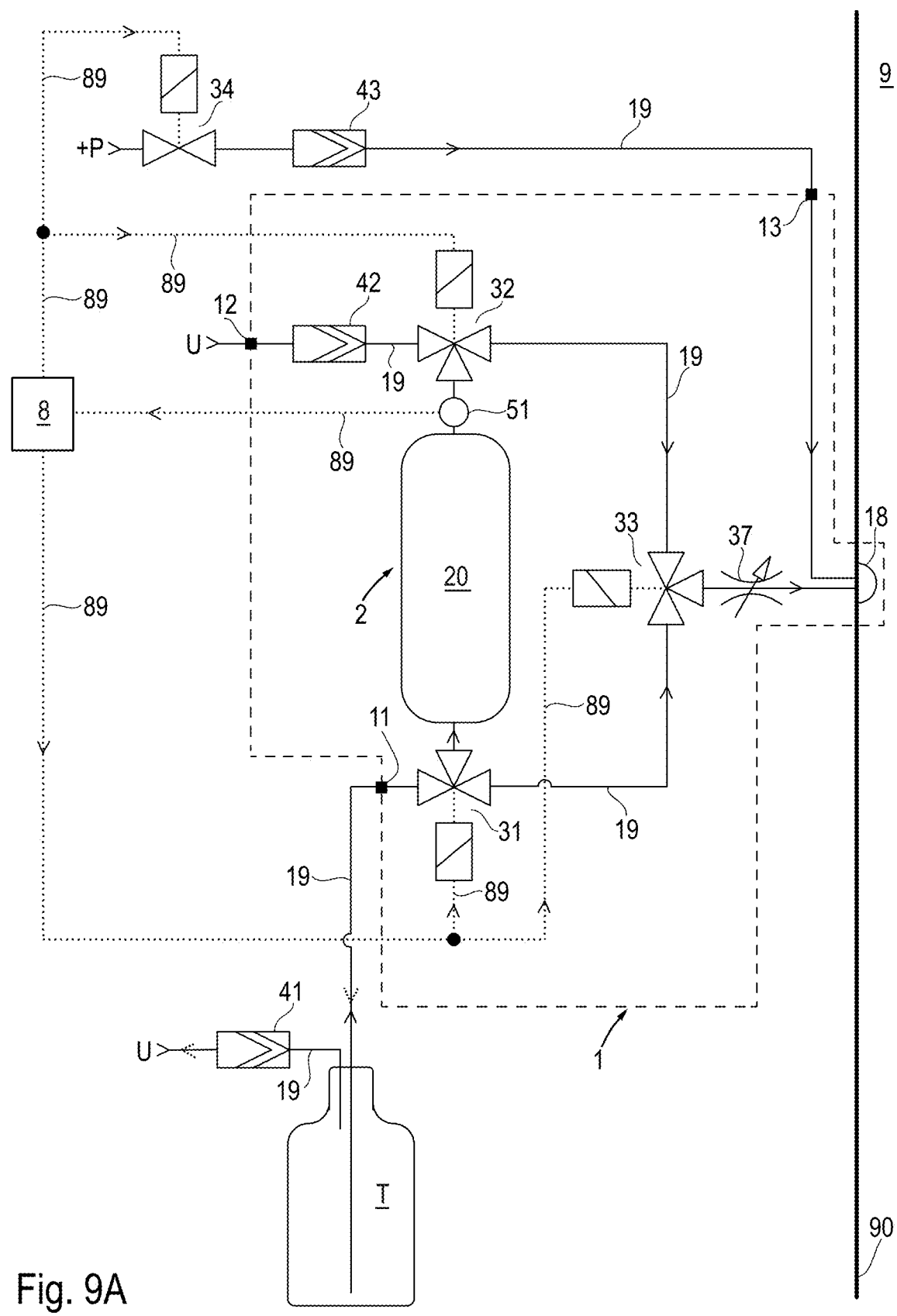
Figure 9B:
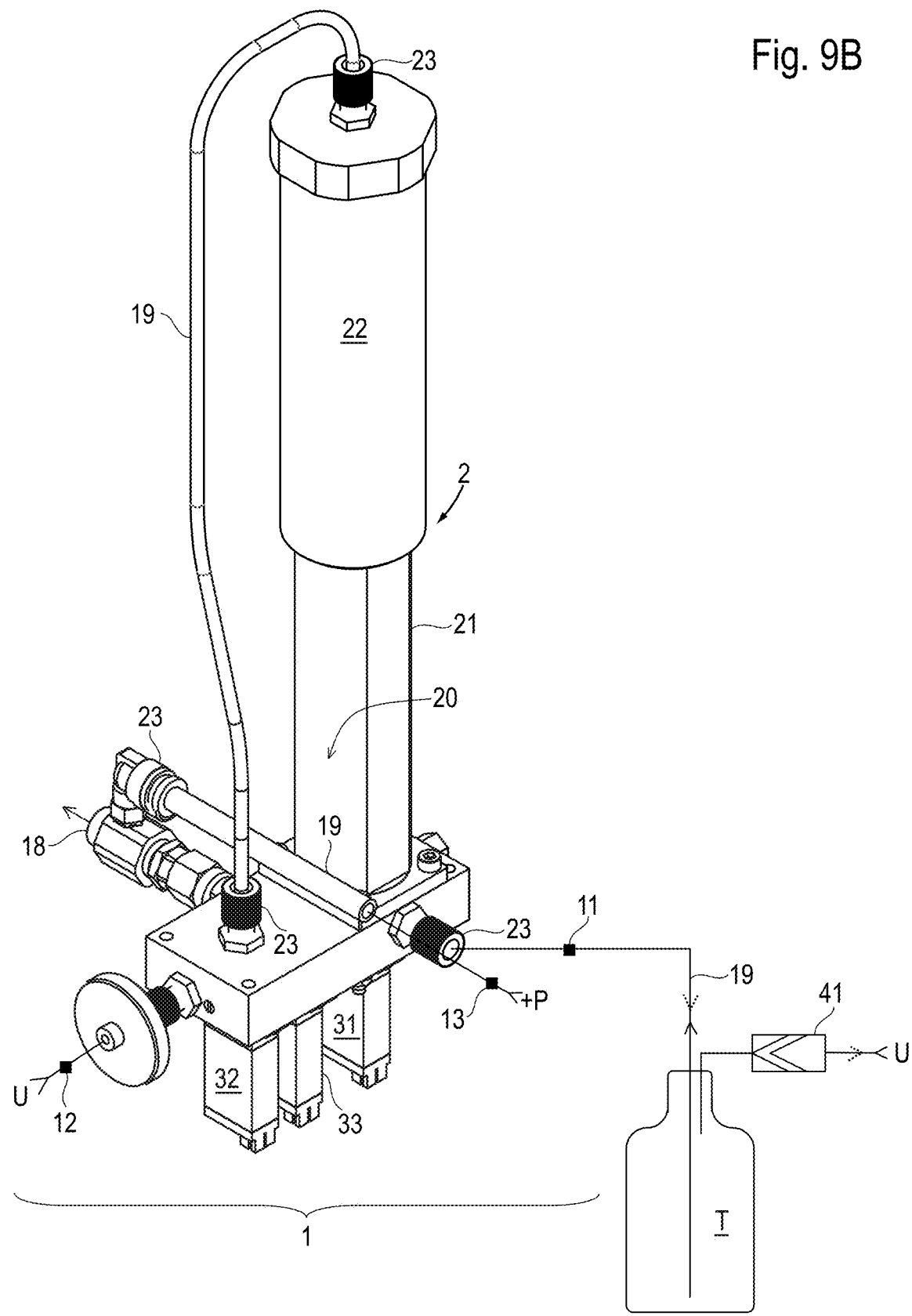
Figure 9G:
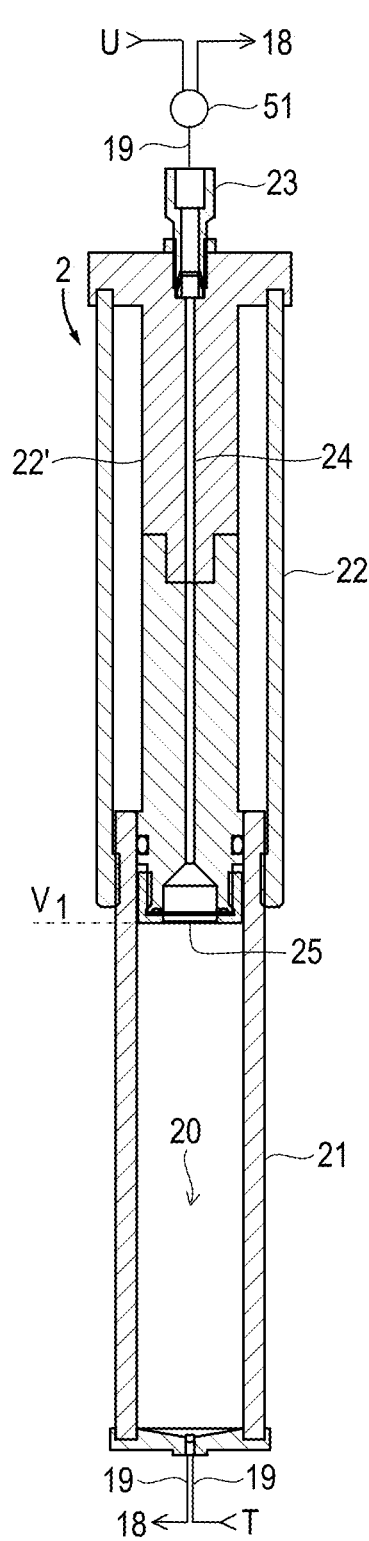
Figure 9H:
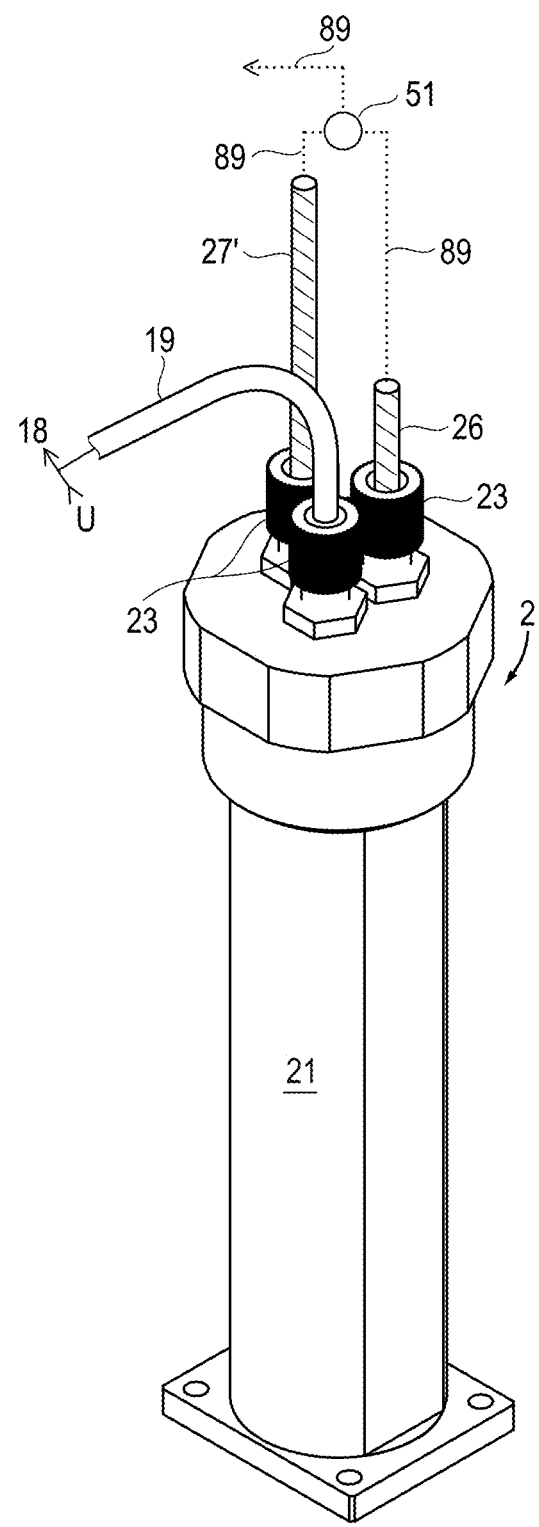
Figure 9J:
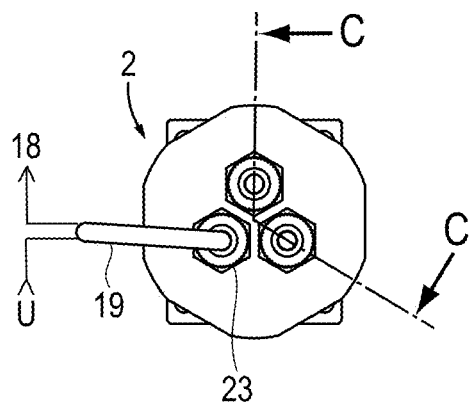

In the drawings shows:

FIG. 1A—the circuit diagram of a first variant of the arrangement;

FIG. 1B—a perspective schematic diagram of the metering apparatus shown in FIG. 1A;

FIG. 1C—a frontal view of the metering apparatus in accordance with FIG. 1B;

FIG. 1D—a lateral view of the metering apparatus in accordance with FIG. 1B;

FIG. 1E—a partial exploded view of the metering apparatus in accordance with FIG. 1B, FIG. 1F—a more detailed exploded view of the metering apparatus in accordance with FIG. 1B, FIG. 1G—an even more detailed exploded view of the metering apparatus in accordance with FIG. 1B, FIG. 1H—the vertical sectional view on the line AA in FIG. 1D, FIG. 1J—the horizontal sectional view on the line BB in FIG. 1D, FIG. 2A—the circuit diagram of a second variant of the arrangement;

FIG. 2B—a perspective schematic diagram of the metering apparatus shown in FIG. 2A;

FIG. 2C—a partial exploded view of the metering apparatus in accordance with FIG. 2B;

FIG. 3A—the circuit diagram of a third variant of the arrangement;

FIG. 3B—a perspective schematic diagram of the metering apparatus shown in FIG. 3A;

FIG. 3C—a partial exploded view of the metering apparatus in accordance with FIG. 3B;

FIG. 4A—the circuit diagram of a fourth variant of the arrangement;

FIG. 4B—a perspective schematic diagram of the metering apparatus shown in FIG. 4A;

FIG. 4C—a partial exploded view of the metering apparatus in accordance with FIG. 4B;

FIG. 5—the circuit diagram of a fifth variant of the arrangement;

FIG. 6—the circuit diagram of a sixth variant of the arrangement;

FIG. 7—the circuit diagram of a seventh variant of the arrangement;

FIG. 8—the circuit diagram of an eighth variant of the arrangement;

FIG. 9A—the circuit diagram of a ninth variant of the arrangement;

FIG. 9B—a perspective schematic drawing of the metering apparatus shown in FIG. 9A with a storage chamber that is adjustable in size and a connected tank for storing decontamination agent;

FIG. 9C—a perspective view of the metering container shown in FIG. 9B with an empty storage chamber in the large volume setting and a spherical closure element as a flotation body;

FIG. 9D—an enlarged vertical sectional view of the metering container in accordance with FIG. 9C, FIG. 9E—the view in accordance with FIG. 9C with a filled storage chamber and small volume setting;

FIG. 9F—an enlarged vertical sectional view of the metering container in accordance with FIG. 9E;

FIG. 9G—a vertical sectional view of the metering container shown in FIG. 9B with a closure element as a semi-permeable membrane;

FIG. 9H—a perspective view of a modified metering container with an electrically adjustable portion size in the storage chamber;

FIG. 9J—a plan view of the structural design in accordance with FIG. 9H; and

Figure 9K:
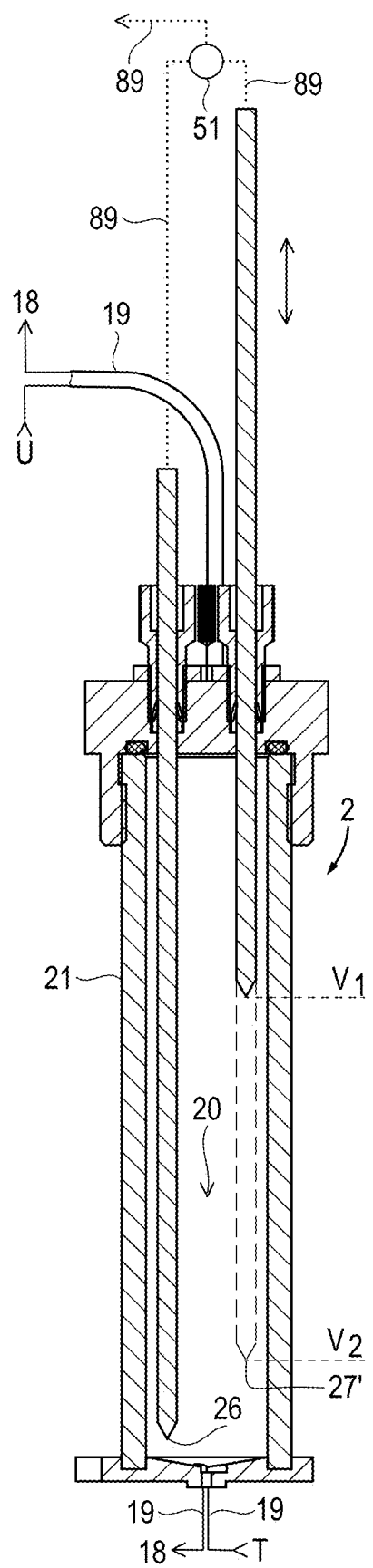

FIG. 9K—the vertical sectional view on the line C-C in FIG. 9J.

EXEMPLARY EMBODIMENT

The detailed description of the arrangement in accordance with the invention for introducing a desired quantity of decontamination agent into a containment facility is provided below with reference to the attached drawings. In so doing, the structural design of a total of nine variants of the arrangement and their function is explained. In the interest of avoiding repetitions, the following statement applies for the description of the individual variants: if reference numerals are provided in a figure sequence that is associated with one variant but not explained in the associated description text, then reference is made to their explanation in the preceding variants.

FIGS. 1A to 1J (First Variant of the Arrangement)

Initially defined on the metering apparatus 1 is a first connection site 11 by means of which a substance line 19 that originates from the tank T leads into the metering apparatus 1, wherein a substance line 19 that forms a feed line from the ambient air U flows into the tank T. Moreover, a second connection site 12, a third connection site 13 and a fourth connection site 14 are provided, by means of which respectively a substance line 19 that originates from the compressed air connection +P leads into the metering apparatus 1. The substance line 19 that continues from the first connection site 11 leads to a first control element 31, simultaneously the first control element 31 is connected via a control line 89 to the control unit 8. The substance line 19 that continues from the second connection site 12 leads to a fifth control element 35, and simultaneously the fifth control element 35 is connected via a control line 89 to the control unit 8. The substance line 19 that continues from the fourth connection site 14 leads to a sixth control element 36, and simultaneously the sixth control element 36 is connected via a control line 89 to the control unit 8. A fourth control element 34 that is connected via a control line 89 to the control unit 8 is installed in the substance line 19 that conveys compressed air +P to the third connection site 13.

A substance line 19 continues from the first control element 31 to the metering container 2 that has the storage chamber 20 arranged therein, said storage chamber being for example in the size of 1 cm³. A further substance line 19 extends from the first control element 31 to the spray nozzle 18 discharging into the containment facility 9, said spray nozzle is inserted into the chamber wall 90 of said containment facility 9. A substance line 19 continues from the fifth control element 35 and extends to a feeder device 7 that flows into the ambient air U and is preferably in the form of a Venturi nozzle. A substance line 19 extends from the third connection site 13 to the spray nozzle 18. A substance line 19 continues from the sixth control element 36 and flows above a fill level sensor 51 into the substance line 19 that leads onwards to the first safety element 61.

A substance line 19 extends from the storage chamber 20 by way of a fill level sensor 51, which is connected via a control line 89 to the control unit 8, onwards to a first safety element 61 and from there to the feeder device 7. An eighth control element 38, preferably in the form of an adjustable restrictor valve, is installed in the substance line 19 between the fifth control element 35 and the feeder device 7. A ninth control element 39, preferably in the form of a restrictor valve, is installed in the substance line 19 between the sixth control element 36 and its junction into the substance line 19 that leads onwards to the first safety element 61. An empty status sensor 52 that is connected via a control line 89 to the control unit 8 is arranged in the substance line 19 between the first control element 31 and the metering container 2. A second safety element 62 is installed in the substance line 19 between the first safety element 61 and the feeder device 7, wherein the two safety elements 61,62 are preferably configured as semi-permeable membranes. The two safety elements 61,62 form a double shielding-arrangement so that decontamination agent does not unintentionally pass by way of the feeder device 7 into the environment U, on the other hand, however, air may be drawn by means of suction into the storage chamber 20.

A seventh control element 37, preferably in the form of an adjustable restrictor valve, is installed in the other substance line 19 between the first control element 31 and the spray nozzle 18. The control elements 37-39 are used to finely adjust the function of the entire arrangement. It is possible to determine the flow resistance of the seventh control element 37, for example by means of the selected flow cross-section and length of the hose connection between the line connections 23 at the housing 10 and at the spray nozzle 18. The through-flow rate of the decontamination agent is optimized by means of the seventh control element 37 in order to realize that said decontamination agent exits the spray nozzle 18 in the form of a fine as possible mist. The eighth control element 38 is used to adjust the output of the feeder device 7 in order to build up the liquid column that is to be maintained from the tank T via the substance line 19 through the storage chamber 20 as far as the first sensor 51, including to overcome the flow resistance that is prevailing along this path.

The tank T, the control unit 8, the source for the compressed air +P and the feed line from the ambient air U are located outside the metering apparatus 1. The metering apparatus 1 that is structured within the connection sites 11-14 is configured in a compact manner (cf. FIGS. 1B to 1J), broken down on a modular basis into a cover 17, below that a housing 10, below that a metering container 2, below that a further housing 10 and at the very bottom the first control element 31. Seals 28 and screws 29 of different dimensions are used to assemble the metering apparatus 1. The two safety elements 62,61 that are held spaced apart from one another by a spacer element 69 are located in the upper housing 10, wherein a funnel 67 is arranged below the first safety element 61. The degassing chamber 15 adjoins the storage chamber 20 at the top and extends into the upper housing 10.

A substance line 19 that originates from the ambient air U flows into the tank T so that, as the decontamination agent is drawn off by means of suction from the tank T, it is possible for air to flow in, and, as the decontamination agent is returned from the line system into the tank T, displaced air may escape into the ambient air U. A first filter 41 is installed in this substance line 19 in order to ensure that only cleaned air passes into the tank T.

During the start-up of the installation, the first control element 31 and the fifth control element 35 receive status pulses from the control unit 8 so as to open the first control element 31 from the tank T to the metering container 2 and to open the fifth control element 35 so as to feed compressed air +P into the feeder device 7, as a result of which decontamination agent is drawn by means of suction into the storage chamber 20 by way of the two safety elements 61,62. As soon as the desired fill level in the storage chamber 20 is realized, the fill level sensor 51 signals this to the control unit 8, as a result of which decontamination agent is no longer drawn off by means of suction from the tank T, the first control element 31 is switched over, the fourth control element 34 is opened and the fifth control element 35 is closed. Consequently, the spray nozzle 18 is supplied with compressed air +P by way of the substance line 19, the Venturi effect is started and thus the portion of decontamination agent that is available in the storage chamber 20, in close proximity to the containment facility 9, is drawn in by means of suction and introduced into the containment facility 9 in aerosol form. A third filter 43 located downstream of the fourth control element 34 guarantees that only pure compressed air +P passes to the spray nozzle 18. If the storage chamber 20 has been emptied, the empty status sensor 52 signals this to the control unit 8 and as required, the storage chamber 20 may be re-filled with the next portion of decontamination agent and its processing then started.

If the desired quantity of required decontamination agent is realized for performing a proper decontamination pro dure of the containment facility 9 with a corresponding number n of portions the path along the substance line 19 from the first control element 31 by way of the seventh control element 37 to the spray nozzle 18 is emptied by means of suction and the line system is to be emptied, the control unit 8 is switched over. The first control element 31 opens the return path from the storage chamber 20 into the tank T. The compressed air +P that is fed in by way of the sixth control element 36 forces the decontamination agent that is still located in the storage chamber 20 and in the adjoining substance lines 19 back into the tank T. In so doing, the ninth control element 39 is used for calculating the required pressure of the compressed air +P that is supplied by way of the sixth control element 36 for the purpose of returning the residual decontamination agent into the tank T.

The metering apparatus 1 is composed essentially from the upper and the lower housing part 10, the metering container 2 that is arranged between said housing parts and the cover 17 that is placed on the top. The line connections 23 are provided for connecting to the respective sections of the substance lines 19. The adjustable seventh control element 37 is formed for example by virtue of selectively dimensioning a substance line 19 of a specific length section and flow cross-section.

FIGS. 2A to 2C (Second Variant of the Arrangement)

This metering apparatus 1 is composed essentially from the one housing part 10, the metering container 2 that is arranged thereon and the cover 17 that is placed on the top. In comparison to the first variant, this arrangement has fewer components. The fourth connection site 14, the sixth control element 36, the ninth control element 39 and the first sensor 51 for signaling the fill level and also the associated sections of substance lines 19 and control lines 89 are omitted. The end of the procedure of feeding portions of decontamination agent into the metering container 2 is controlled in this case on a time basis in that the fifth control element 35 is closed and subsequently the first control element 31 is switched to feed the spray nozzle 18. While the metering container 2 is being emptied also while decontamination agent is being returned into the tank T air flows by way of the feeder device 7 through the two safety elements 62,61 so as to compensate the volume in the metering container 2. After the process of decontaminating the container facility 9 in the proper manner has been terminated, any decontamination agent remaining in the arrangement is returned into the tank T in this case not by means of pressure and suction but rather merely by virtue of the force of gravity on account of the height difference with respect to the tank T positioned below.

FIGS. 3A to 3C (Third Variant of the Arrangement)

This metering apparatus 1 is even more compact with the housing part 10, the metering container 2 that is arranged therein and the cover 17 that is placed on the top. In comparison to the second variant, the second safety element 62 is omitted in this case, in lieu of the second sensor 52 for detecting the empty status of the metering container 2 there is now only the first sensor 51 for detecting the fill level, and the size of the storage chamber 20 in the pot-like metering container 2 is now adjustable, for example between 1 cm$^3$ and 50 cm$^3$. The adjustability is realized by means of a stand pipe 27 that protrudes into the storage chamber 20 and is height adjustable.

The feeder device 7 that is influenced with compressed air +P by way of the open fifth control element 35 causes in turn decontamination agent to be drawn by means of suction out of the tank T by way of the first control element 31 into the metering container 2 until the first sensor 51 indicates that the fill volume has realized the set fill volume, upon which the first control element 31 switches over so as to feed the spray nozzle 18. Any decontamination agent remaining in the arrangement is returned into the tank T merely by virtue of the force of gravity.

FIGS. 4A to 4C (Fourth Variant of the Arrangement)

Also, this metering apparatus 1 is very compact with the housing part 10, the metering container 2 that is arranged therein and the cover 17 that is placed on the top. In order to fasten the first sensor 51, a mounting plate 16 that is to be screwed to the housing 10 is provided in addition. The single difference with respect to the structural design of the third variant is that in lieu of the previously used metering container 2 having the storage chamber 20 with an adjustable storage volume, in the case of this exemplary embodiment the size of the storage chamber 20 is defined by virtue of dimensioning a hose winding or tubing winding. Depending upon the inner cross-section and length of the winding, it is possible to form a storage volume of for example between 1 cm$^3$ and 5 cm$^3$. As in the case in the third variant, the metering container 2 is filled with decontamination agent that is fed into the containment facility 9 by way of the spray nozzle 18 and any decontamination agent remaining in the arrangement is returned to the tank T.

FIG. 5 (Fifth Variant of the Arrangement)

In relation to the fourth variant, the fifth control element 35 and the feeder device 7 are omitted, only a second control element 32 is installed in lieu of these fittings. A control line 89 leads from the control unit 8 to the second control element 32 and a substance line 19 leads out of the ambient air U through the second connection site 12 by way of the first safety element 61 and the seventh control element 37.

The adjustable seventh control element 37 is used to adjust the quantity of incoming air as the storage chamber 20 empties. The second safety element 62 is now positioned between the first sensor 51 for indicating the filled storage chamber 20 and the second control element 32. Moreover, a third sensor 53 is installed between the junction of the substance line 19, which originates from the second control element 32, into the substance line 19 that leads to the spray nozzle 18, and said third sensor signals the absence of decontamination agent, in particular the portion of decontamination agent from the metering container 2 is processed by way of the spray nozzle 18.

The storage chamber 20 is now filled with decontamination agent from the tank T solely by means of the suction effect of the spray nozzle 18 by way of the second control element 32 and the second safety element 62. The first safety element 61 is used as a filter for the air incoming from the environment U into the substance line 19 and simultaneously as a barrier in the event that, as a result of a defect, decontamination agent should penetrate into this section of the substance line 19, said decontamination agent is consequently unable to pass into the environment U. The second safety element 62 is installed quasi upstream of the first safety element 61. Any decontamination agent remaining in the arrangement is also returned into the tank T in this case by virtue of the force of gravity.

FIG. 6 (Sixth Variant of the Arrangement)

In the case of this exemplary embodiment, decontamination agent that is drawn off by means of suction from the storage chamber 20 is no longer fed to the spray nozzle 18 by way of the second control element 32 but rather by way of the open fifth control element 35 in the case of the first sensor 51 signaling the fill level. While decontamination agent is being supplied to the spray nozzle 18, the first control element 31 with the substance line 19 leading to the tank T is closed, whereas the control element with the substance line 19 leading to the ambient air U is open. The section of the substance line 19 leads from the ambient air U initially through the second connection site 12, the first safety element 61 being connected downstream of said second connection site 12. The adjustable seventh control element 37 is arranged in the substance line 19 between the first safety element 61 and the connection to the first control element 31, wherein the first safety element 61 and the seventh control element 37 have the function as previously described (cf. FIG. 5).

Conversely, if the first sensor 51 does not signal the presence of decontamination agent but rather signals the presence of air, this indicates that the storage chamber 20 is either completely empty or not yet completely filled. Consequently, the fifth control element 35 is closed or remains closed and the first control element 31 is open towards the tank T but closed towards the ambient air U. In the case that compressed air +P is continuously supplied by way of the fourth control element 34, the suction effect that is generated by the spray nozzle 18 through the second safety element 62 and through the storage chamber 20 refills or completely fills said storage chamber with a next portion n of decontamination agent. However, the second safety element 62 does not allow any possibly entrained particles of decontamination agent to pass through. Any decontamination agent remaining in the arrangement flows in turn solely by virtue of the force of gravity into the tank T.

FIG. 7 (Seventh Variant of the Arrangement)

This exemplary embodiment is simplified with respect to the structural design of the sixth variant. The section of the substance line 19, which is routed in the bypass and has the fifth control element 35 installed therein, and the second control element 62 are omitted. Apart from the reduced level of safety, the operating principle is virtually identical.

In the case that the first sensor 51 signals the fill level, in accordance with pulses from the control unit 8, the first control element 31 is closed towards the tank T and open towards the ambient air U. The spray nozzle 18 that is influenced with compressed air +P by way of the fourth control element 34 and the third filter 43 causes decontamination agent to be drawn in by means of suction from the filled storage chamber 20 and said decontamination agent is fed into the containment facility 9 in an atomized form.

Conversely, if the first sensor 51 signals only the presence of air the storage chamber 20 is thus empty or not completely filled the first control element 31 is opened or remains open towards the tank T and closed towards the ambient air U. The compressed air +P that is supplied to the spray nozzle 18 by way of the fourth control element 34 generates a suction effect that acts on the storage chamber 20 and as a result generates its next fill with a further portion n of decontamination agent that is then available for feeding into the containment facility 9. Any decontamination agent remaining in the arrangement is returned into the tank T on the basis of the force of gravity.

FIG. 8 (Eighth Variant of the Arrangement)

The structural design of this exemplary embodiment represents an obvious variation with respect to the fifth variant. In lieu of the hose winding or tubing winding that is provided for dimensioning the size of the storage chamber 20, the top-like metering container 2 that has an adjustable storage volume for example between 1 cm³ and 50 cm³ is used. The third sensor 53 is omitted and the first safety element 61 is now arranged at the position of the second safety element 62, namely between the first sensor 51 and the second control element 32. In addition, the adjustable seventh control element 37 is now arranged in the substance line 19 between the first control element 31 and the junction of the substance line 19 that originates from the second control element 32 into the first control element 31.

At the start of the filling mode, the first sensor 51 detects that the fill level of the storage chamber 20 is insufficient. The control unit 8 causes the first control element 31 to open namely from the storage chamber 20 only towards the tank T, and said control unit causes the second control element 32 to open namely from the spray nozzle 18 only towards the storage chamber 20 with the result that the suction effect from the spray nozzle 18 that is influenced by compressed air +P extends by way of the storage chamber 20 as far as into the tank T and the storage chamber 20 is successively filled with decontamination agent.

The end of the process of filling the storage chamber 20 is detected by the first sensor 51 and processed by way of the control unit 8 with the result that a switch-over is performed. The first control element 31 changes into the open position now only from the storage chamber 20 towards the spray nozzle 18, and the second control element 32 changes into the open position now from the ambient air U only more towards the storage chamber 20. As a result, according to the flow resistance set at the seventh control element 37, decontamination agent that is drawn in by means of suction from the spray nozzle 18 flows at a corresponding through-flow rate and in an atomized form into the containment facility 9. Any decontamination agent remaining in the arrangement flows back into the tank T owing to the effect of the force of gravity.

FIGS. 9A to 9K (Ninth Variant of the Arrangement)

Reference is made to the eighth variant for a comparison of the structural design of this arrangement. The storage chamber 20 of the metering container 2 is in turn adjustable, for example it has a storage volume between 1 cm³ and 50 cm³.

The substance line 19 extends from the tank T through the first connection site 11 to the first control element 31 that is configured as a 3-way valve and from said first control element a connection leads by way of the substance line 19 to the metering container 2 and a further connection leads by way of a substance line 19 to the third control element 33. A substance line 19 extends from the third control element 33 in the form of a 3-way valve towards the second control element 32 that is likewise a 3-way valve, and a further connection leads by way of the substance line 19 towards the spray nozzle 18. The adjustable seventh control element 37 is arranged between the third control element 33 and the spray nozzle 18. As is the case in all previous variants, the substance line 19 leads from a compressed air connection +P through the third connection site 13 to the spray nozzle 18. The fourth control element 34 and the third filter 43 are arranged in the substance line 19 between the compressed air connection +P and the third connection site 13. A connection of the second control element 32 flows with the first fill level sensor 51 that is connected therebetween into the metering container 2 and a further connection of this control element 32 extends as a substance line 19 through the second connection site 12, which has a second filter 42 that is connected upstream, towards the ambient air U. The fill level sensor 51 and the four control elements 31-34 are connected to the control unit 8 by way of control lines 89.

As the storage chamber 20 is being filled, the first control element 31 is only open from the metering container 2 towards the tank T but is in the closed position towards the third control element 33. Another connection of the third control element 33 is open towards the second control element 32 and from there onwards to the metering container 2. The remaining connection of the third control element 33 extends open by way of the seventh control element 37 to the spray nozzle 18, where the suction of the decontamination agent is generated. The remaining connection of the second control element 32 is simultaneously closed towards the ambient air U.

As the first sensor 51 detects that the set fill level in the storage chamber 20 has been realized, the arrangement is switched over to the start in the spray mode. The connection at the first control element 31 is closed from the metering container 2 to the tank T and the connection to the third control element 33 is opened. Simultaneously, the connection from the third control element 33 towards the second control element 32 is closed and the connection from the second control element 32 by way of the second connection site 12 towards the ambient air U is opened, with the result that the decontamination agent that is drawn in by means of suction from the storage chamber 20 successively by the spray nozzle 18 that is influenced with compressed air +P may be replaced by incoming air. In this situation, the connection coming from the storage chamber 20 via the first control element 31 and further via the third control element 33 and the seventh control element 37 is open towards the spray nozzle 18. Any decontamination agent remaining in the arrangement is also returned into the tank T in this case solely by virtue of the force of gravity.

In accordance with FIGS. 9B to 9G, the adjustability of the fill volume of the storage chamber 20 of the metering container 2 is based on a cylindrical body having a lower base part 21, in which is arranged the storage chamber 20, and on a lifting part 22 that slides in a telescopic manner over the base part 21. The lifting part 22 comprises a piston 22' that protrudes in an axial manner into the storage chamber 20 and as the lifting part 22 moves further over the base part 21 changes the size of the storage chamber 20, for example between a larger volume $V_1$ and a smaller volume $V_2$. When the storage chamber 20 is in the empty state, a closure element 25 in FIGS. 9C to 9F a floatation ball lies on the bottom of the base part 21. As the storage chamber 20 is successively filled, the closure element 25 floats upwards until the desired level is realized, at which point the closure element 25 blocks the funnel-shaped junction of the duct 24 that extends in an axial manner through the piston 22'.

In the case of the embodiment of the metering container 2 in accordance with FIG. 9G, in lieu of the spherical closure element 25 that is based on a floatation principle, a closure element 25 in the form of a semi-permeable membrane is arranged upstream of the funnel-shaped junction of the duct 24 that extends in an axial manner through the piston 22' and said semi-permeable membrane prevents decontamination agent passing into the duct 24. At the base part 21, a substance line 19 leads from the tank T or from the spray nozzle 18 into the storage chamber 20. On the other hand, a substance line 19 leads from the outlet of the duct 24 starting at the line connection 23 to the fill level sensor 51 and from there finally to the ambient air U or to the spray nozzle 18.

In the case of the embodiment of the metering container 2 in accordance with FIGS. 9H to 9K, only the base part 21 is provided and an electrical probe 27', which has an adjustable insertion depth, adjusts the portion size in the storage chamber 20, for example between a larger volume $V_1$ and a smaller volume $V_2$. In the case of a completely empty storage chamber 20 or where the fill level has not yet been realized, the electrical contact 26 and the electrical probe 27' are not covered, which is detected by the first sensor 51. Conversely, when the fill level is realized, the electrical contact 26 and the electrical probe 27' are covered, which is registered by the first sensor 51. The feed system into the base part 21 is equivalent to that in FIG. 9B to 9G. A substance line 19 that leads finally to the ambient air U or to the spray nozzle 18 extends from a separate line connection 23 that flows into the storage chamber 20.

The invention claimed is:

1. An arrangement for introducing a desired quantity of decontamination agent into a containment facility comprising:
    a) a tank as a storage vessel for storing the decontamination agent in liquid form;
    b) a metering apparatus having a spray nozzle that is directed into the containment facility so as to atomize the decontamination agent;
    c) a compressed air connection and a control unit so as to operate the metering apparatus, wherein
    d) the metering apparatus has a metering container that comprises a storage chamber that has a defined volume for receiving an individual portion of decontamination agent, characterized in that the storage chamber:
        a) is configured with a fixed or adjustable size;
        b) is provided as a separate container, a cylinder, a recess in the metering container or as an extended or drawn tube length; and
        c) the storage chamber has a volume in the range of 1 $cm^3$ to 50 $cm^3$,
    e) the storage chamber is provided so as to successively receive a number (n) of portions of decontamination agent from the tank and the portion that is respectively held in the storage chamber is provided so as to be introduced by means of the spray nozzle into the containment facility prior to receiving a subsequent portion, wherein the number (n) of portions for realizing the desired quantity of required decontamination agent may be selected between 1 and a whole number multiple of 1; and
    wherein in order to be able to adjust the size of the portion of decontamination agent that may be held in the storage chamber:
        a) a standpipe, a piston or an electrical probe, which may be inserted into the storage chamber and whose position may be adjusted; or
        b) a hose winding or tubing winding with a specific inner cross-section and length of winding are used.

2. The arrangement as claimed in claim 1, wherein:
    a) the compressed air connection is used to fill the storage chamber with decontamination agent from the tank and to operate the spray nozzle based on the Venturi principle; and
    b) the metering apparatus comprises a feeder device for filling the storage chamber with decontamination agent from the tank.

3. The arrangement as claimed in claim 2, wherein a fill level sensor, a closure element or an adjustable standpipe, an adjustable piston or an adjustable electrical probe are used so as to signal that a complete portion of decontamination agent has been supplied into the storage chamber and to terminate the supply from the tank.

4. The arrangement as claimed in claim 3, wherein:
    a) the closure element is provided as a floatation body that is arranged in the storage chamber or as a semi-permeable membrane; and
    b) the adjustable electrical probe cooperates with a fixed electrical contact, both of which are covered by the decontamination agent when a complete portion of decontamination agent has been supplied.

5. The arrangement as claimed in claim 4, wherein it is possible to program into the control unit:
a) the time sequence with the start, the process flow and the termination of the procedure of introducing the desired quantity of decontamination agent into the containment facility; and
b) the desired quantity by virtue of determining the number (n) of portions.

6. The arrangement as claimed in claim 5, wherein it is possible to program into the control unit that after the process of introducing the desired quantity of decontamination agent into the containment facility has been terminated any decontamination agent remaining in the metering apparatus is returned to the tank.

7. The arrangement as claimed in claim 6, wherein:
a) in order to introduce the desired quantity of decontamination agent into the containment facility, the following are provided for controlling the process flow and the metered quantity:
   aa) a first category of control elements in the form of 3-way valves which are influenced by the control unit by way of control lines and are installed in substance lines that convey decontamination agent or ambient air;
   ab) a second category of control elements in the form of stop valves which are influenced by the control unit by way of control lines and are installed in substance lines that convey decontamination agent or ambient air; and
   ac) a third category of control elements in the form of restrictor valves, which are installed in substance lines that convey decontamination agent or compressed air; and
b) the compressed air and ambient air that are supplied into the arrangement flow through cleaning filters.

8. The arrangement as claimed in claim 7, wherein:
a) the metering apparatus is designed as a compact assembly and may be installed in close proximity to the containment facility in order to realize a minimal length of the substance line from the storage chamber to the spray nozzle and consequently to realize a minimal transportation time for the decontamination agent that is supplied in portions from the storage chamber to the spray nozzle; and
b) the tank, the source for the compressed air and the control unit are located outside the metering apparatus; wherein
c) a central control unit that is already provided for the containment facility may be used as a control unit for the metering apparatus or alternatively it is possible to provide a separate control unit that is integrated into the metering apparatus.

9. The arrangement as claimed in claim 8, wherein defined on the metering apparatus are:
a) a first connection site by means of which a substance line that originates from the tank leads into the metering apparatus, wherein a substance line that forms a feed line from the ambient air discharges into the tank; and
b) a second connection site, a third connection site and a fourth connection site, by means of which respectively a substance line that originates from the compressed air connection leads into the metering apparatus.

10. The arrangement as claimed in claim 9, wherein:
a) the metering apparatus further comprises:
   aa) a first control element wherein the substance line that continues from the first connection site leads to said first control element and said first control element is connected by way of a control line to the control unit;
   ab) a second control element wherein the substance line that continues from the second connection site leads to said second control element and said second control element is connected by way of a control line to the control unit; and
   ac) a third control element wherein the substance line that continues from the fourth connection site leads to said third control element and said third control element is connected by way of a control line to the control unit; and
b) a fourth control element that is connected via a control line to the control unit is installed in the substance line that conveys compressed air to the third connection site.

11. The arrangement as claimed in claim 10, wherein:
a) a substance line continues from the first control element to the metering container that has the storage chamber arranged therein, and a further substance line extends from the first control element to the spray nozzle;
b) a substance line continues from the second control element and extends to a feeder device that discharges into the ambient air;
c) a substance line extends from the third connection site to the spray nozzle;
d) a substance line extends from the fourth control element and discharges above a fill level sensor into the substance line that leads onwards to the first safety element.

12. The arrangement as claimed in claim 11, wherein:
a) a substance line extends from the storage chamber via a fill level sensor, which is connected via a control line to the control unit, onwards to a first safety element and from there to the feeder device;
b) an fifth control element, is installed in the substance line between the fifth control element and the feeder device; and
c) a sixth control element, is installed in the substance line between the sixth control element and its junction into the substance line that leads onwards to the first safety element.

13. The arrangement as claimed in claim 12, wherein:
a) an empty status sensor that is connected via a control line to the control unit is installed in the substance line between the first control element and the metering container;
b) a second safety element is installed in the substance line between the first safety element and the feeder device; and
c) a seventh control element, is provided in the other substance line between the first control element and the spray nozzle.

14. The arrangement as claimed in claim 1, wherein the volume of the storage chamber is in the range of 1 $cm^3$ to 5 $cm^3$.

15. The arrangement as claimed in claim 7, wherein the restrictor valves are adjustable.

16. The arrangement as claimed in claim 11, wherein the substance line that continues from the second control element to the feeder device is in the form of a Venturi nozzle.

17. The arrangement as claimed in claim 12, wherein the fifth control element is in the form of an adjustable restrictor valve.

18. The arrangement as claimed in claim 12, wherein the sixth control element is in the form of a restrictor valve.

19. The arrangement as claimed in claim 13, wherein the seventh control element is in the form of an adjustable restrictor valve.

20. The arrangement as claimed in claim 13, wherein the two safety elements are configured as semi-permeable membranes.

* * * * *